United States Patent
Jung et al.

(10) Patent No.: US 11,911,749 B2
(45) Date of Patent: Feb. 27, 2024

(54) CHROMIUM CATALYST PRECURSOR, ETHYLENE OLIGOMERIZATION CATALYST INCLUDING THE SAME, AND METHOD OF PREPARING ETHYLENE OLIGOMER

(71) Applicant: SK Innovation Co., Ltd., Seoul (KR)

(72) Inventors: Il Gu Jung, Daejeon (KR); Hyo Seung Park, Daejeon (KR); Jun Soo Son, Daejeon (KR); Myung Jin Kim, Daejeon (KR); Jong Chan Kim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 17/890,424

(22) Filed: Aug. 18, 2022

(65) Prior Publication Data
US 2023/0100188 A1 Mar. 30, 2023

(30) Foreign Application Priority Data
Aug. 19, 2021 (KR) ........................ 10-2021-0109387

(51) Int. Cl.
*B01J 31/18* (2006.01)
*B01J 31/22* (2006.01)
*C07C 2/26* (2006.01)

(52) U.S. Cl.
CPC ......... *B01J 31/189* (2013.01); *B01J 31/2234* (2013.01); *C07C 2/26* (2013.01); *B01J 2231/20* (2013.01); *B01J 2531/0208* (2013.01); *B01J 2531/62* (2013.01); *C07C 2531/24* (2013.01)

(58) Field of Classification Search
CPC .. B01J 31/189; B01J 31/2234; B01J 2231/20; B01J 2531/0208; B01J 2531/62; B01J 31/2409; B01J 31/143; B01J 31/146; C07C 2/26; C07C 2531/24; C07C 2/32; C07C 2/34; C07C 2/36; C07C 11/02; C07C 11/107; Y02P 20/52; C07F 5/02; C07F 11/00; C07F 19/00
See application file for complete search history.

(56) References Cited

U.S. PATENT DOCUMENTS

| | | | |
|---|---|---|---|
| 7,511,183 B2 | 3/2009 | Blann et al. | |
| 2012/0041241 A1 | 2/2012 | Ewart et al. | |
| 2018/0071725 A1* | 3/2018 | Klosin | ............... C07F 9/65844 |
| 2019/0308178 A1 | 10/2019 | Lee et al. | |

FOREIGN PATENT DOCUMENTS

| | | |
|---|---|---|
| JP | S4948308 B1 | 12/1974 |
| WO | 2010092554 A1 | 8/2010 |

OTHER PUBLICATIONS

Nakano et al., "Ligand exchanging reactions of M(acac)3 (M=Cr or Co) in Lewis acidic conditions", Inorganica Chimica Acta, 2003, pp. 202-208, vol. 343.

Kim et al., "MAO-free and extremely active catalytic system for ethylene tetramerization", Appl Organometal Chem., 2019, pp. 1-13, vol. 33, No. e4829.

Rucklidge et al., "Ethylene Tetramerization with Cationic Chromium(I) Complexes", Organometallics, 2007, pp. 2782-2787, vol. 26, No. 10.

* cited by examiner

*Primary Examiner* — Ali Z Fadhel
(74) *Attorney, Agent, or Firm* — The Webb Law Firm

(57) ABSTRACT

Provided are a chromium catalyst precursor, an ethylene oligomerization catalyst including the same, and a method of preparing an ethylene oligomer using the same. More particularly, a chromium catalyst precursor which may oligomerize ethylene with high activity and high selectivity in spite of not using methylaluminoxane (MAO) or modified-methylaluminoxane (MMAO), an oligomerization catalyst including the same, and a method of preparing an ethylene oligomer using the same are provided.

19 Claims, No Drawings

CHROMIUM CATALYST PRECURSOR, ETHYLENE OLIGOMERIZATION CATALYST INCLUDING THE SAME, AND METHOD OF PREPARING ETHYLENE OLIGOMER

CROSS-REFERENCE TO RELATED APPLICATION

This application claims priority to Korean Patent Application No. 10-2021-0109387, filed Aug. 19, 2021, the disclosure of which is hereby incorporated by reference in its entirety.

BACKGROUND OF THE INVENTION

Field of the Invention

The following disclosure relates to a chromium catalyst precursor, an ethylene oligomerization catalyst including the same, and a method of preparing an ethylene oligomer using the same, and more particularly, to a chromium catalyst precursor which may oligomerize ethylene with high activity and high selectivity in spite of not using methylaluminoxane (MAO) or modified-methylaluminoxane (MMAO), an oligomerization catalyst including the same, and a method of preparing an ethylene oligomer using the same.

Description of Related Art

An ethylene oligomer, specifically, 1-hexene or 1-octene is an important commercial raw material which is widely used in a polymerization process as a monomer or comonomer for preparing a linear low-density polyethylene, and is obtained by purifying a product produced by an oligomerization reaction of ethylene.

However, a conventional ethylene oligomerization reaction has an inefficient aspect, such as producing significant amounts of butene, higher oligomers, and polyethylene together with 1-hexene and 1-octene. Since the conventional ethylene oligomerization technology as such generally produces various α-olefins depending on a Schulze-Flory or Poisson product distribution, the contents of 1-hexene and 1-octene in the product are relatively low.

Recently, a study to produce 1-hexene by selectively trimerizing ethylene or to produce 1-octene by selectively tetramerizing ethylene by transition metal catalysis has been conducted, and most of the known transition metal catalysts are chromium-based catalysts.

As a representative example of selective oligomerization of ethylene, a method of selectively producing 1-octene and 1-hexene, using a catalyst system formed of a chromium trivalent compound ($CrCl_3$ or $Cr(acac)_3$), i-$PrN(PPh_2)_2$ which is a bisphosphine ligand, and methylaluminoxane (MAO) has been reported (U.S. Pat. No. 7,511,183B2).

However, the catalyst system has a problem of implementing high activity catalytic performance only when expensive methylaluminoxane (MAO) is used excessively, and a problem of producing a large amount of polyethylene (PE). In addition, since catalytic activity is decreased at a high temperature, the produced amount and the selectivity of an olefin, in particular, 1-octene, are decreased, and the production of PE as a by-product is increased, and thus, tube blockage and fouling occur to inevitably cause process interruption, thereby causing a serious problem in an olefin polymerization process.

Thus, many efforts have been made to replace MAO with an uncoordinated anion, in order to develop a catalyst system which does not use expensive methylaluminoxane (MAO). However, it has low activity or needs a separate process such as separation purification as compared with most catalyst systems using MAO, and thus, is inappropriate for commercial use.

As an example using a catalyst system which does not use MAO, it has been reported that after a chromium-phosphine complex is prepared and separated, an aluminum anion having steric hindrance (soft aluminum anion) is additionally reacted to implement oligomer reaction activity (Organometallics 2007, 26, 2782-2787), but since the activity is as low as about 50% as compared with a MAO cocatalyst system of the same ligand and expensive aluminum anion raw material is used, it may be inappropriate for actual commercial application.

As another example using a borate cocatalyst instead of MAO, it has been reported that a chromium (III) precursor is mixed with triethylaluminum (TEAL), a PNP ligand, and a borate cocatalyst, which is then used as a catalyst without a separation process to implement an oligomer reaction activity (WO 2010/092554 A1), but since an expensive chromium precursor such as $Cr(2\text{-ethylhexanoate})_3$ and a borate cocatalyst having very low solubility such as anilinium borate are used, there may be a limitation in the preparation and use of a catalyst solution.

In addition, it has been reported that triethylaluminum (TEAL), a boron cocatalyst, and a chromium (III) precursor are successively reacted to synthesize a catalyst precursor, and a catalyst prepared by reacting a PNP ligand is separated to implement an oligomer reaction activity (Appl Organometal Chem. 2019; e4829), but a separation process is needed after synthesis of a catalyst due to a complicated process, and since an applicable PNP ligand structure is limited, there may be a limitation in the preparation and use of a catalyst.

Therefore, the development of a catalyst, a catalyst system, or an oligomerization method which allows the use of low-cost raw materials and application of various ligands, does not use MAO, and oligomerizes ethylene with high activity and high selection to prepare 1-hexene and 1-octene, and also, may reduce occurrence of a polyethylene by-product which is not desired, is needed.

SUMMARY OF THE INVENTION

An embodiment of the present invention is directed to providing a chromium catalyst precursor which may oligomerize ethylene with high activity and high selectivity in spite of not using methylaluminoxane (MAO) or modified-methylaluminoxane (MMAO), and an oligomerization catalyst including the same.

Another embodiment of the present invention is directed to providing a chromium catalyst precursor which may oligomerize ethylene with high activity and high selectivity without deterioration of activity over a long period of time due to excellent stability, and an oligomerization catalyst including the same.

Still another embodiment of the present invention is directed to providing a method of oligomerizing ethylene which may oligomerize ethylene with high activity and high selectivity to prepare 1-hexene and 1-octene in a high yield, in spite of not using methylaluminoxane (MAO) or modified-methylaluminoxane (MMAO).

In one general aspect, a precursor of an ethylene oligomerization catalyst which may oligomerize ethylene with high activity and high selectivity in spite of not using methylaluminoxane (MAO) or modified-methylaluminoxane (MMAO) is provided, and the catalyst precursor of the present invention may be a chromium catalyst precursor represented by the following Chemical Formula 1:

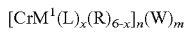  [Chemical Formula 1]

wherein $M^1$ is a Group 13 element;

L is a ligand in a β-keto enolate form;

R is a halogen, $C_1$-$C_{10}$ alkoxy, or $C_6$-$C_{20}$ aryloxy;

w is a neutral coordination ligand;

n is an integer of 1 or 2;

x is an integer of 1 to 6; and m is an integer of 0 to 4.

In the chromium catalyst precursor according to an exemplary embodiment, $M^1$ may be boron (B) or aluminum (Al).

In the chromium catalyst precursor according to an exemplary embodiment, L may be an enolate-based ligand represented by the following Chemical Formula A:

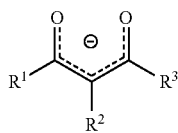  [Chemical Formula A]

wherein $R^1$ and $R^3$ are independently of each other a halogen, hydrocarbyl, substituted hydrocarbyl, heterohydrocarbyl, or substituted heterohydrocarbyl;

$R^2$ is hydrogen, a halogen, hydrocarbyl, substituted hydrocarbyl, heterohydrocarbyl, or substituted heterohydrocarbyl; and $R^1$ and $R^2$ or $R^3$ and $R^2$ may be linked by hydrocarbylene, substituted hydrocarbylene, heterohydrocarbylene, or substituted heterohydrocarbylene to form a ring.

In the chromium catalyst precursor according to an exemplary embodiment, W may be a nitrile having 2 to 30 carbon atoms, a cyclic or acyclic ether having 2 to 30 carbon atoms, or water ($H_2O$), and preferably may be acetonitrile (ACN), tetrahydrofuran (THF), diethyl ether, or water ($H_2O$).

In the chromium catalyst precursor according to an exemplary embodiment, $M^1$ may be boron (B) or aluminum (Al); R may be a halogen or $C_1$-$C_{10}$ alkoxy; W may be acetonitrile (ACN), tetrahydrofuran (THF), diethyl ether, or water ($H_2O$); m may be an integer of 2 to 4; x may be an integer of 1 to 6; and L may be an acac-based ligand having the following structure:

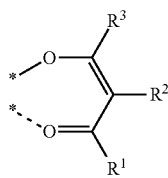

wherein $R^1$ and $R^3$ are independently of each other $C_1$-$C_{10}$ alkyl or $C_6$-$C_{20}$ aryl, and the alkyl and the aryl of $R^1$ and $R^3$ may be further substituted by one or more substituents selected from halogens, $C_1$-$C_{10}$ alkyl, $C_6$-$C_{20}$ aryl, halo$C_1$-$C_{10}$ alkyl, and halo$C_6$-$C_{20}$ aryl;

$R^2$ is hydrogen, a halogen, $C_1$-$C_{10}$ alkyl, or $C_6$-$C_{20}$ aryl, and the alkyl and the aryl of $R^2$ may be further substituted by one or more selected from halogens, $C_1$-$C_{10}$ alkyl, $C_6$-$C_{20}$ aryl, halo$C_1$-$C_{10}$ alkyl, and halo$C_6$-$C_{20}$ aryl; and $R^1$ and $R^2$ or $R^3$ and $R^2$ may be linked by $C_3$-$C_{10}$ alkylene, $C_3$-$C_{10}$ alkenylene, $C_6$-$C_{20}$ arylene, $C_3$-$C_{10}$ heteroalkylene, $C_3$-$C_{10}$ heteroalkenylene, or $C_6$-$C_{20}$ heteroarylene to form a ring.

In the chromium catalyst precursor according to an exemplary embodiment, $M^1$ may be boron (B); L may be acetylacetonate (ACAC); R may be $C_1$-$C_{10}$ alkoxy; W may be acetonitrile (ACN), tetrahydrofuran (THF), diethyl ether, or water ($H_2O$); m may be an integer of 2 to 4; and x may be an integer of 1 to 6.

In the chromium catalyst precursor according to an exemplary embodiment, $M^1$ may be aluminum (Al); L may be acetylacetonate (ACAC); R may be a halogen; W may be acetonitrile (ACN), tetrahydrofuran (THF), diethyl ether, or water ($H_2O$); m may be an integer of 2 to 4; and x may be an integer of 1 to 6.

In another general aspect, an ethylene oligomerization catalyst which may oligomerize ethylene with high activity and high selectivity in spite of not using methylaluminoxane (MAO) or modified-methylaluminoxane (MMAO) is provided, and the ethylene oligomerization catalyst of the present invention includes a chromium catalyst precursor represented by Chemical Formula 1 and a heteroatom ligand.

In the ethylene oligomerization catalyst according to an exemplary embodiment, the heteroatom ligand may be a phosphine ligand, represented by the following Chemical Formula 3:

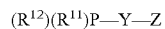  [Chemical Formula 3]

wherein $R^{11}$ and $R^{12}$ are independently of each other hydrocarbyl, heterohydrocarbyl, substituted hydrocarbyl, or substituted heterohydrocarbyl;

Y is a linking group between P and Z;

Z is *—P($R^{13}$)($R^{14}$) or

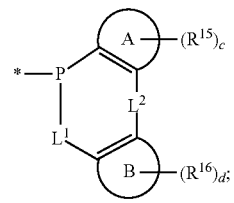

ring A and ring B are independently of each other an aromatic ring;

$L^1$ and $L^2$ are independently of each other a single bond, a heteroatom, a substituted heteroatom, —C(=O)—, or —CR'R"—;

R' and R" are independently of each other hydrogen, hydrocarbyl, substituted hydrocarbyl, heterohydrocarbyl, or substituted heterohydrocarbyl;

$R^{13}$ to $R^{16}$ are independently of one another hydrocarbyl, heterohydrocarbyl, substituted hydrocarbyl, or substituted heterohydrocarbyl; and c and d are independently of each other an integer of 0 to 4.

In the ethylene oligomerization catalyst according to an exemplary embodiment, the heteroatom ligand may be represented by Chemical Formula 3 wherein Y is hydrocarbylene, —N($R^{21}$)—, —N($R^{21}$)—N($R^{22}$)—, =C($R^{23}$)—N($R^{21}$)—, —N($R^{21}$)—C($R^{23}$)($R^{24}$)—, or —N($R^{21}$)-$L^3$-N($R^{22}$)—; $R^{21}$ to $R^{24}$ are independently hydrogen, hydrocarbyl, substituted hydrocarbyl, heterohydrocarbyl, substituted heterohydrocarbyl, or a substituted heteroatom; and $L^3$ is hydrocarbylene.

In the ethylene oligomerization catalyst according to an exemplary embodiment, the heteroatom ligand of Chemical Formula 3 may be a heteroatom ligand having a P—N—P skeletal structure represented by the following Chemical Formula 4 or 5:

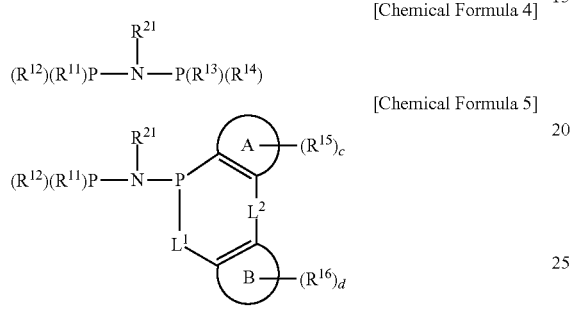

[Chemical Formula 4]

[Chemical Formula 5]

wherein

Ring A and Ring B are independently of each other a $C_6$-$C_{20}$ aromatic ring;

$R^{11}$ to $R^{14}$, $R^{15}$, and $R^{16}$ are independently of each other $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_1$-$C_{10}$ alkyl, $C_2$-$C_{10}$ alkenyl, $C_2$-$C_{10}$ alkynyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, $C_3$-$C_{10}$ cycloalkyl, mercapto$C_1$-$C_{10}$ alkyl, mercapto$C_2$-$C_{10}$ alkenyl, mercapto$C_2$-$C_{10}$ alkynyl, $C_3$-$C_{20}$ heteroaryl, 5-membered to 7-membered heterocycloalkyl, —N$R^{a1}R^{b1}$ or —Si$R^{c1}R^{d1}R^{e1}$;

$R^{a1}$ and $R^{b1}$ are independently of each other hydrogen, $C_1$-$C_{10}$ alkyl, $C_2$-$C_{10}$ alkenyl, $C_2$-$C_{10}$ alkynyl, $C_6$-$C_{20}$ aryl, $C_1$-$C_{10}$ alkylamino, $C_2$-$C_{10}$ alkenylamino, or $C_2$-$C_{10}$ alkynylamino;

$R^{c1}$ is $C_1$-$C_{10}$ alkyl, $C_2$-$C_{10}$ alkenyl, $C_2$-$C_{10}$ alkynyl, or $C_6$-$C_{20}$ aryl;

$R^{d1}$ and $R^{e1}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;

$R^{21}$ is $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_3$-$C_{10}$ cycloalkyl, $C_3$-$C_{20}$ heteroaryl, 5-membered to 7-membered heterocycloalkyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, —N$R^{a2}R^{b2}$, or —Si$R^{c2}R^{d2}R^{e2}$;

$L^1$ and $L^2$ are independently of each other a single bond, —O—, —S—, —NR'—, —P(=O)R'—, —P(=Se)R'—, —P(=S)R'—, —SiR'R''—, —CR'R''—, or —C(=O)—;

R' and R'' are independently of each other hydrogen, $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_3$-$C_{10}$cycloalkyl, $C_3$-$C_{20}$ heteroaryl, 5-membered to 7-membered heterocycloalkyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, —N$R^{a3}R^{b3}$, or —Si$R^{c3}R^{d3}R^{e3}$;

$R^{a2}$, $R^{b2}$, $R^{a3}$, and $R^{b3}$ are independently of one another hydrogen, $C_1$-$C_{10}$ alkyl, $C_2$-$C_{10}$ alkenyl, $C_2$-$C_{10}$ alkynyl, or $C_6$-$C_{20}$ aryl;

$R^{c2}$ and $R^{c3}$ are independently of each other $C_1$-$C_{10}$ alkyl, $C_2$-$C_{10}$ alkenyl, $C_2$-$C_{10}$ alkynyl, or $C_6$-$C_{20}$ aryl;

$R^{d2}$, $R^{e2}$, $R^{d3}$, and $R^{e3}$ are independently of one another hydrogen, $C_1$-$C_{10}$ alkyl, $C_2$-$C_{10}$ alkenyl, $C_2$-$C_{10}$ alkynyl, or $C_6$-$C_{20}$ aryl;

c and d are independently of each other an integer of 0 to 4; and the aryl, the arylalkyl, the alkyl, the arylalkenyl, the alkenyl, the arylalkynyl, the alkynyl, the alkoxy, the aryloxy, the cycloalkyl, the heteroaryl, or the heterocycloalkyl of $R^{11}$ to $R^{14}$, $R^{15}$, and $R^{16}$, and the alkyl, the alkenyl, the aryl, the aralkyl, the aralkenyl, the aralkynyl, the cycloalkyl, the heteroaryl, the heterocycloalkyl, the alkoxy, the aryloxy, the alkoxycarbonyl, the alkylcarbonyloxy, the alkenylcarbonyloxy, the alkynylcarbonyloxy, the aminocarbonyl, the alkylcarbonylamino, the alkenylcarbonylamino, or the alkynylcarbonylamino of $R^{21}$, R', and R'' may be further substituted by one or more selected from the group consisting of halogens, $C_1$-$C_{10}$ alkyl, halo$C_1$-$C_{10}$ alkyl, $C_2$-$C_{10}$ alkenyl, $C_2$-$C_{10}$ alkynyl, $C_1$-$C_{10}$ alkoxy, halo$C_1$-$C_{10}$ alkoxy, $C_6$-$C_{20}$ aryl, $C_6$-$C_{20}$ aryloxy, 5-membered to 7-membered heterocycloalkyl, —N$R^{a4}R^{b4}$, and —Si$R^{c4}R^{d4}R^{e4}$; and $R^{a4}$ and $R^{b4}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl, and $R^{c4}$ to $R^{e4}$ are independently of each other $C_1$-$C_{10}$ alkyl or $C_1$-$C_{10}$ alkoxy.

In the ethylene oligomerization catalyst according to an exemplary embodiment, the heteroatom ligand may be represented by Chemical Formulae 3 to 5 wherein $L^1$ and $L^2$ are independently of each other a single bond or —O—.

In the ethylene oligomerization catalyst according to an exemplary embodiment, the heteroatom ligand of Chemical Formula 3 may be a heteroatom ligand represented by the following Chemical Formula 6:

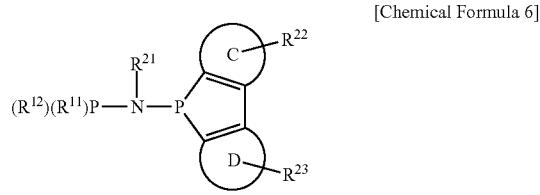

[Chemical Formula 6]

wherein $R^{11}$ and $R^{12}$ are independently of each other $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_1$-$C_{10}$ alkyl, $C_2$-$C_{10}$ alkenyl, $C_2$-$C_{10}$ alkynyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, $C_3$-$C_{10}$ cycloalkyl, mercapto$C_1$-$C_{10}$ alkyl, mercapto$C_2$-$C_{10}$ alkenyl, mercapto$C_2$-$C_{10}$ alkynyl, $C_3$-$C_{20}$ heteroaryl, 5-membered to 7-membered heterocycloalkyl, —NR$^{a1}$R$^{b1}$, or —SiR$^{c1}$R$^{d1}$R$^{e1}$;

R$^{a1}$ and R$^{b1}$ are independently of each other hydrogen, $C_1$-$C_{10}$ alkyl, $C_2$-$C_{10}$ alkenyl, $C_2$-$C_{10}$ alkynyl, $C_6$-$C_{20}$ aryl, $C_1$-$C_{10}$ alkylamino, $C_2$-$C_{10}$ alkenylamino, or $C_2$-$C_{10}$ alkynylamino;

R$^{c1}$ is $C_1$-$C_{10}$ alkyl, $C_2$-$C_{10}$ alkenyl, $C_2$-$C_{10}$ alkynyl, or $C_6$-$C_{20}$ aryl;

R$^{d1}$ and R$^{e1}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;

R$^{21}$ is $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_3$-$C_{10}$ cycloalkyl, $C_3$-$C_{20}$ heteroaryl, 5-membered to 7-membered heterocycloalkyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, —NR$^{a2}$R$^{b2}$, or —SiR$^{c2}$R$^{d2}$R$^{e2}$;

R$^{a2}$ and R$^{b2}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;

R$^{c2}$ is $C_1$-$C_{10}$ alkyl, $C_2$-$C_{10}$ alkenyl, $C_2$-$C_{10}$ alkynyl, or $C_6$-$C_{20}$ aryl;

R$^{d2}$ and R$^{e2}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;

ring C and ring D are independently of each other benzene or naphthalene;

R$^{22}$ and R$^{23}$ are hydrogen, $C_1$-$C_{10}$ alkyl, $C_6$-$C_{20}$ aryl, $C_3$-$C_{10}$ cycloalkyl, $C_6$-$C_{20}$ aryl$C_1$-$C_{10}$ alkyl, or $C_1$-$C_{10}$ alkyl$C_6$-$C_{20}$ aryl; and the aryl, the arylalkyl, the alkyl, the arylalkenyl, the alkenyl, the arylalkynyl, the alkynyl, the alkoxy, the aryloxy, the cycloalkyl, the heteroaryl, and the heterocycloalkyl of R$^{11}$ and R$^{12}$, and the alkyl, the alkenyl, the aryl, the aralkyl, the aralkenyl, the aralkynyl, the cycloalkyl, the heteroaryl, the heterocycloalkyl, the alkoxy, the aryloxy, the alkoxycarbonyl, the alkylcarbonyloxy, the alkenylcarbonyloxy, the alkynylcarbonyloxy, the aminocarbonyl, the alkylcarbonylamino, the alkenylcarbonylamino, or the alkynylcarbonylamino of R$^{21}$ may be further substituted by one or more selected from the group consisting of halogens, $C_1$-$C_{10}$ alkyl, halo$C_1$-$C_{10}$ alkyl, $C_2$-$C_{10}$ alkenyl, $C_2$-$C_{10}$ alkynyl, $C_1$-$C_{10}$ alkoxy, halo$C_1$-$C_{10}$ alkoxy, $C_6$-$C_{20}$ aryl, $C_6$-$C_{20}$ aryloxy, 5-membered to 7-membered heterocycloalkyl, —NR$^{a4}$R$^{b4}$, and —SiR$^{c4}$R$^{d4}$R$^{e4}$; and R$^{a4}$ and R$^{b4}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl, and R$^{c4}$ to R$^{e4}$ are independently of each other $C_1$-$C_{10}$ alkyl or $C_1$-$C_{10}$ alkoxy.

In the ethylene oligomerization catalyst according to an exemplary embodiment, the chromium catalyst precursor may be represented by Chemical Formula 1 in which M$^1$ is boron (B) or aluminum (Al); R is a halogen or $C_1$-$C_{10}$ alkoxy; W is acetonitrile (ACN), tetrahydrofuran (THF), diethyl ether, or water ($H_2O$); m is an integer of 2 to 4; x is an integer of 1 to 6; and L is an acac-based ligand having the following structure:

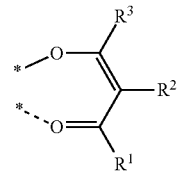

wherein R$^1$ and R$^3$ are independently of each other $C_1$-$C_{10}$ alkyl or $C_6$-$C_{20}$ aryl, and the alkyl and the aryl of R$^1$ and R$^3$ may be further substituted by one or more substituents selected from halogens, $C_1$-$C_{10}$ alkyl, $C_6$-$C_{20}$ aryl, halo$C_1$-$C_{10}$ alkyl, and halo$C_6$-$C_{20}$ aryl;

R$^2$ is hydrogen, a halogen, $C_1$-$C_{10}$ alkyl, or $C_6$-$C_{20}$ aryl, and the alkyl and the aryl of R$^2$ may be further substituted by one or more selected from halogens, $C_1$-$C_{10}$ alkyl, $C_6$-$C_{20}$ aryl, halo$C_1$-$C_{10}$ alkyl, and halo$C_6$-$C_{20}$ aryl; and R$^1$ and R$^2$ or R$^3$ and R$^2$ may be linked by $C_3$-$C_{10}$ alkylene, $C_3$-$C_{10}$ alkenylene, $C_6$-$C_{20}$ arylene, $C_3$-$C_{10}$ heteroalkylene, $C_3$-$C_{10}$ heteroalkenylene, or $C_6$-$C_{20}$ heteroarylene to form a ring.

In still another general aspect, a method of preparing an ethylene oligomer includes: bringing a catalyst system including the ethylene oligomerization catalyst and an organoboron compound-based cocatalyst into contact with an ethylene monomer to prepare an ethylene oligomer.

In the method of preparing an ethylene oligomer according to an exemplary embodiment, the organoboron compound-based cocatalyst may be an organoboron compound represented by the following Chemical Formula 9:

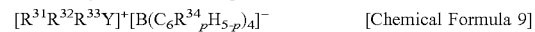

[Chemical Formula 9]

wherein

Y is C or NH;

R$^{31}$ to R$^{33}$ are independently of one another hydrogen, $C_1$-$C_{20}$ alkyl, or $C_6$-$C_{20}$ aryl, and the alkyl or the aryl of R$^{31}$ may be further substituted by one or more selected from the group consisting of $C_1$-$C_{20}$ alkyl and $C_6$-$C_{20}$ aryl;

R$^{34}$ is fluoro, $C_1$-$C_{20}$ alkyl, or $C_1$-$C_{20}$ alkoxy, and the alkyl or the alkoxy of R$^{34}$ may be further substituted by one or more fluoro(s); and p is an integer of 3 to 5.

In the method of preparing an ethylene oligomer according to an exemplary embodiment, the catalyst system may further include an alkylaluminum compound represented by the following Chemical Formula 10:

[Chemical Formula 10]

wherein

R$_{41}$ is $C_1$-$C_{20}$ alkyl; and

R$^{42}$ and R$^{43}$ are independently of each other $C_1$-$C_{20}$ alkyl or a halogen.

In the method of preparing an ethylene oligomer according to an exemplary embodiment, the ethylene oligomer may be 1-hexene, 1-octene, or a mixture thereof.

In the method of preparing an ethylene oligomer according to an exemplary embodiment, a hydrocarbon-based solvent may be used as a reaction solvent in ethylene oligomerization.

Other features and aspects will be apparent from the following detailed description, the drawings, and the claims.

DESCRIPTION OF THE INVENTION

Hereinafter, the present invention will be described, however, technical terms and scientific terms used herein have the general meaning understood by those skilled in the art to which the present invention pertains unless otherwise defined, and a description for the known function and configuration which may unnecessarily obscure the gist of the present invention will be omitted in the following description.

It should be understood that in the present specification, unless otherwise required in the context, the terms "comprise" and "comprising" include a suggested step or constituent element, or a group of steps or constituent elements, but imply that any other step or constituent element or any group of steps or constituent groups is not excluded.

In the present specification, "substituent", "radical", "group", "moiety", and "fragment" may be used interchangeably.

In the present specification, "$C_A$-$C_B$" refers to "the number of carbons being A or more and B or less".

In the present specification, "hydrocarbyl" or "heterohydrocarbyl" refers to a radical having one binding site derived from hydrocarbon or heterohydrocarbon, and "hetero" means that a carbon atom is substituted by one or more heteroatoms selected from O, S, Se, P, B, and N atoms.

In the present specification, "alkyl", "alkoxy", and other substituents including an "alkyl" part include both straight chain and branched chain forms.

In the present specification, "substituted" refers to a group or a site having one or more substituents attached to a structural skeleton of a group or a part. It means that any one or more selected from deuterium, hydroxy, halogen, alkyl, haloalkyl, alkenyl, alkynyl, alkoxy, haloalkoxy, aryl, aryloxy, haloaryl, heterocycloalkyl, carboxyl, cyano, nitro, alkylaryl, arylalkyl, arylalkenyl, arylalkynyl, cycloalkyl, cycloalkylalkyl, cycloalkenyl, heteroaryl, heteroarylalkyl, —N(R')$_2$, —Si(R")$_3$, —COR'", —OCOR'", —NHCOR'", and —SR' [R' is independently of each other hydrogen, alkyl, alkenyl, alkynyl, or aryl, R" is independently of each other hydrogen, alkyl, alkenyl, alkynyl, alkoxy, or aryl, and R'" is hydrogen, alkyl, alkenyl, alkynyl, alkoxy, aryl, or amino] are substituted on the group or the structural skeleton mentioned without a limitation.

Specifically, "substituted" refers to being substituted by any one or more selected from deuterium, hydroxy, halogen, $C_1$-$C_{10}$ alkyl, halo$C_1$-$C_{10}$ alkyl, $C_2$-$C_{10}$ alkenyl, $C_2$-$C_{10}$ alkynyl, $C_1$-$C_{10}$ alkoxy, halo$C_1$-$C_{10}$ alkoxy, $C_6$-$C_{20}$ aryl, $C_6$-$C_{20}$ aryloxy, halo$C_6$-$C_{20}$ aryl, 5-membered to 7-membered heterocycloalkyl, carboxyl, cyano, nitro, $C_1$-$C_{10}$ alkyl$C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_3$-$C_{10}$ cycloalkyl, $C_3$-$C_{10}$ cycloalkyl$C_1$-$C_{10}$ alkyl, $C_3$-$C_{10}$ cycloalkenyl, $C_3$-$C_{20}$ heteroaryl, $C_3$-$C_{20}$ heteroaryl$C_1$-$C_{10}$ alkyl, —N(R')$_2$, —Si(R")$_3$, —COR'", —OCOR'", —NHCOR'", and —SR' [R' is independently of each other hydrogen, $C_1$-$C_{10}$ alkyl, $C_2$-$C_{10}$ alkenyl, $C_2$-$C_{10}$ alkynyl, or $C_6$-$C_{20}$ aryl, R" is independently of each other hydrogen, $C_1$-$C_{10}$ alkyl, $C_2$-$C_{10}$ alkenyl, $C_2$-$C_{10}$ alkynyl, $C_1$-$C_{10}$ alkoxy, or $C_6$-$C_{20}$ aryl, and R'" is hydrogen, $C_1$-$C_{10}$ alkyl, $C_2$-$C_{10}$ alkenyl, $C_2$-$C_{10}$ alkynyl, $C_1$-$C_{10}$ alkoxy, $C_6$-$C_{20}$ aryl, or amino].

In the present specification "alkyl" refers to a monovalent straight-chain or branched-chain saturated hydrocarbon radical consisting of only carbon and hydrogen atoms, and may include methyl, ethyl, propyl, isopropyl, butyl, isobutyl, t-butyl, pentyl, hexyl, octyl, nonyl, or the like, but is not limited thereto. In addition, an alkyl radical described in the present invention has 1 to 10, preferably 1 to 7, and more preferably 1 to 5 carbon atoms.

In the present specification, "aryl" refers to a monovalent organic radical derived from an aromatic hydrocarbon by removal of one hydrogen, including a single- or fused ring system containing, as an example, 4 to 7, preferably 5 or 6 ring atoms in each ring, and even a form in which a plurality of aryls are linked by a single bond. A specific example thereof includes phenyl, naphthyl, biphenyl, anthryl, indenyl, fluorenyl, and the like, but is not limited thereto. In addition, an alkyl radical described in the present invention has 6 to 20, preferably 6 to 12 carbon atoms.

In the present specification, "halo" or "halogen" refers to a fluorine, chlorine, bromine, or iodine atom.

In the present specification, "alkenyl" is a straight-chain or branched-chain unsaturated hydrocarbon monovalent radical containing one or more double bonds between two or more carbon atoms, and specifically, includes ethenyl, propenyl, prop-2-en-2-yl, 1-butenyl, 2-butenyl, isobutenyl, 1-pentenyl, 2-pentenyl, 3-methyl-1-butenyl, 2-methyl-2-butenyl, 2,3-dimethyl-2-butenyl, and the like, but is not limited thereto.

In the present specification, "alkynyl" is a straight-chain or branched-chain unsaturated hydrocarbon monovalent radical containing one or more triple bonds between two or more carbon atoms, and specifically, includes ethynyl, propynyl, 1-butynyl, 2-butynyl, 1-pentynyl, 2-pentynyl, 3-methyl-1-butynyl, and the like, but is not limited thereto.

In the present specification, "alkoxy" refers to an —O-alkyl radical, in which "alkyl" is as defined above. An example of the alkoxy radical includes methoxy, ethoxy, isopropoxy, butoxy, isobutoxy, t-butoxy, or the like, but is not limited thereto.

In the present specification, "aryloxy" refers to an —O-aryl radical, in which "aryl" is as defined above. An example of the aryloxy radical includes phenoxy, naphthoxy, and the like, but is not limited thereto.

In the present specification, "alkoxycarbonyl" refers to an alkoxy-C(=O) alkoxy radical, in which "alkoxy" is as defined above. An example of the alkoxycarbonyl radical includes methoxycarbonyl, ethoxycarbonyl, isopropoxycarbonyl, propoxycarbonyl, butoxycarbonyl, isobutoxycarbonyl, t-butoxycarbonyl, and the like, but is not limited thereto.

In the present specification, "alkylcarbonyloxy" refers to an —OC(=O)alkyl radical, in which "alkyl" is as defined above. An example of the alkylcarbonyloxy radical includes methylcarbonyloxy, ethylcarbonyloxy, isopropylcarbonyloxy, propylcarbonyloxy, butylcarbonyloxy, isobutylcarbonyloxy, t-butylcarbonyloxy, and the like, but is not limited thereto.

In the present specification, "alkenylcarbonyloxy" refers to an —OC(=O) radical, in which "alkenyl" is as defined above. An example of the alkenylcarbonyloxy radical includes ethenylcarbonyloxy, butenylcarbonyloxy, and the like, but is not limited thereto.

In the present specification, "alkynylcarbonyloxy" refers to —OC(=O)alkynyl radical, in which "alkynyl" is as defined above. An example of the alkynylcarbonyloxy radical includes ethynylcarbonyloxy, butynylcarbonyloxy, and the like, but is not limited thereto.

In the present specification, "cycloalkyl" refers to a monovalent saturated carbocyclic radical formed of one or more rings. An example of the cycloalkyl radical includes cyclopropyl, cyclobutyl, cyclopentyl, cyclopentyl, cycloheptyl, and the like, but is not limited thereto.

In the present specification, "heteroaryl" refers to a monovalent radical of a heteroaromatic ring which is an aryl group containing 1 to 4 heteroatoms selected from N, O, and S as an aromatic ring skeletal atom, and carbons as remaining aromatic ring skeletal atoms, and is a 5- or 6-membered monocyclic heteroaryl and a polycyclic heteroaryl fused with one or more benzene rings, which may be partially saturated. In addition, the heteroaryl in the present invention also includes a form in which one or more heteroaryls are linked by a single bond. An example of the heteroaryl group includes pyrrolyl, pyrazolyl, quinolyl, isoquinolyl, pyridyl, pyrimidinyl, oxazolyl, thiazolyl, thiadiazolyl, triazolyl, imidazolyl, benzimidazolyl, isooxazolyl, benzisooxazolyl, thiophenyl, benzothiophenyl, furyl, benzofuryl, or the like, but is not limited thereto.

In the present specification, "heterocycloalkyl" is a monovalent radical of a 5-membered to 7-membered non-aromatic heterocycle containing 1 to 4 heteroatoms selected from N, O, and S, and the non-aromatic heterocycle is included in a saturated or unsaturated monocycle form, and may be linked through a heteroatom or a carbon atom. An example of the heterocycloalkyl radical may include monovalent radicals of a non-aromatic heterocycle such as pyrrolidine, piperidine, tetrahydropiperidine, piperazine, morpholine, and thiomorpholine.

In the present specification, an alkyl or alkoxy radical may have 1 to 10 carbon atoms, preferably 1 to 7 carbon atoms, and more preferably 1 to 5 carbon atoms, an alkenyl or alkynyl radical may have 2 to 10 carbon atoms, preferably 2 to 7 carbon atoms, and more preferably 2 to 5 carbon atoms, an aryl radical may have 6 to 20 carbon atoms, and preferably 6 to 12 carbon atoms, and a heteroaryl radical may have 3 to 20 carbon atoms, and preferably 3 to 12 carbon atoms.

In the present specification, "ethylene oligomerization" is oligomerization of ethylene, and may be referred to as trimerization and tetramerization depending on the number of ethylene to be polymerized. In particular, in the present specification, it refers to preparation of 1-hexene, 1-octene, or a mixture thereof which is the main comonomer of LLDPE from ethylene.

In the present specification, an "oligomerization catalyst" is defined as including a mixed form of a chromium catalyst precursor and a heteroatom ligand, as well as a chromium complex form with a heteroatom ligand.

In the present specification, an "oligomerization catalyst system" is defined as further including a cocatalyst and/or an additive in the "oligomerization catalyst" described above.

The present inventors found that when a chromium catalyst precursor formed in a specific reaction order using low-cost reactants is applied to an ethylene oligomerization reaction with an organoboron-based cocatalyst, high activity equivalent to that of a conventional oligomerization catalyst system using a large amount of expensive methylaluminoxane (MAO) or modified-methylaluminoxane (MMAO) is implemented to selectively produce 1-octene and 1-hexene, thereby completing the present invention.

The present invention provides a precursor of an ethylene oligomerization catalyst which may oligomerize ethylene with high activity and high selectivity in spite of not using methylaluminoxane (MAO) or modified-methylaluminoxane (MMAO), and the catalyst precursor of the present invention may be a chromium catalyst precursor represented by the following Chemical Formula 1:

[CrM¹(L)$_x$(R)$_{6-x}$]$_n$(W)$_m$     [Chemical Formula 1]

wherein
M¹ is a Group 13 element;
L is a ligand in a β-keto enolate form;
R is a halogen, C$_1$-C$_{10}$ alkoxy, or C$_6$-C$_{20}$ aryloxy;
W is a neutral coordination ligand;
n is an integer of 1 or 2;
x is an integer of 1 to 6; and
m is an integer of 0 to 4.

The chromium catalyst precursor of Chemical Formula 1 may be a reaction product of a chromium (III) precursor represented by Cr(L)$_3$ and a Lewis acid containing a Group 13 element represented by M1(R)$_3$, and the reaction thereof may be performed in an inert solvent. That is, the chromium catalyst precursor may be prepared from easily available low-cost raw materials and be present in a homogeneous solution phase. The inert solvent may be, specifically, a nitrile solvent having 2 to 30 carbon atoms, a cyclic or acyclic ether solvent having 2 to 30 carbon atoms, or water (H$_2$O), or a hydrocarbon solvent containing water. More specifically, it may be acetonitrile (ACN), tetrahydrofuran (THF), diethyl ether, or water (H$_2$O), or chlorobenzene, toluene, or the like containing a small amount of water.

Specifically, the chromium catalyst precursor may be a product obtained by reacting a chromium (III) precursor and a Lewis acid containing a Group 13 element at the same equivalent ratio in an inert solvent.

Since the chromium catalyst precursor may be present in a homogeneous solution phase, its storage stability over a long period of time is very good, it may be activated later into an organoboron-based cocatalyst as an ethylene oligomerization catalyst with a heteroatom ligand to stably maintain catalytic activity in oligomerization, and it is easily applied to a continuous process.

In the chromium catalyst precursor according to an exemplary embodiment, the chromium catalyst precursor of Chemical Formula 1 may be mononuclear or binuclear.

In the chromium catalyst precursor according to an exemplary embodiment, the chromium catalyst precursor of Chemical Formula 1 may include a mononuclear form represented by the following Chemical Formula 1-1:

CrM¹(L)$_x$(R)$_{6-x}$     [Chemical Formula 1-1]

wherein M¹, L, and R are as defined in Chemical Formula 1 above.

In the chromium catalyst precursor according to an exemplary embodiment, the chromium catalyst precursor of Chemical Formula 1 may include a binuclear form represented by the following Chemical Formula 1-2:

[Cr$_2$(L)$_2$(R)$_2$]$^{2+}$[M¹(R)$_2$(L)$_2$]$^-$$_2$(W)$_m$     [Chemical Formula 1-2]

wherein M¹, L, R, W, and m are as defined in Chemical Formula 1 above.

In the chromium catalyst precursor according to an exemplary embodiment, M¹ may be boron (B) or aluminum (Al).

In the chromium catalyst precursor according to an exemplary embodiment, L may be an enolate-based ligand represented by the following Chemical Formula A:

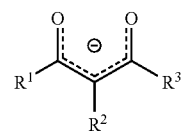

[Chemical Formula A]

wherein
R¹ and R³ are independently of each other a halogen, hydrocarbyl, substituted hydrocarbyl, heterohydrocarbyl, or substituted heterohydrocarbyl;
R² is hydrogen, a halogen, hydrocarbyl, substituted hydrocarbyl, heterohydrocarbyl, or substituted heterohydrocarbyl; and R[1] and R[2] or R[3] and R[2] may be linked by hydrocarbylene, substituted hydrocarbylene, heterohydrocarbylene, or substituted heterohydrocarbylene to form a ring.

In the chromium catalyst precursor according to an exemplary embodiment, W comes from an inert solvent in which a reaction of chromium (III) acetylacetonate and a Lewis acid containing a Group 13 element represented by $M^1(R)_3$ occurs, and is preferably nitrile having 2 to 30 carbon atoms, a cyclic or acyclic ether having 2 to 30 carbon atoms, or water ($H_2O$), and is more preferably acetonitrile (ACN), tetrahydrofuran (THF), diethyl ether or water ($H_2O$).

Preferably, in the chromium catalyst precursor according to an exemplary embodiment, $M^1$ may be boron (B) or aluminum (Al); R may be a halogen or $C_1$-$C_{10}$ alkoxy; W may be acetonitrile (ACN), tetrahydrofuran (THF), diethyl ether, or water ($H_2O$); m may be an integer of 2 to 4; x may be an integer of 1 to 6; and L may be an acac-based ligand having the following structure:

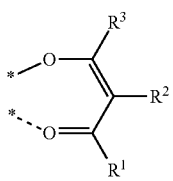

wherein $R^1$ and $R^3$ are independently of each other $C_1$-$C_{10}$ alkyl or $C_6$-$C_{20}$ aryl, and the alkyl and the aryl of $R^1$ and $R^3$ may be further substituted by one or more substituents selected from halogens, $C_1$-$C_{10}$ alkyl, $C_6$-$C_{20}$ aryl, halo$C_1$-$C_{10}$ alkyl, and halo$C_6$-$C_{20}$ aryl;

$R^2$ is hydrogen, a halogen, $C_1$-$C_{10}$ alkyl, or $C_6$-$C_{20}$ aryl, and the alkyl and the aryl of $R^2$ may be further substituted by one or more selected from halogens, $C_1$-$C_{10}$ alkyl, $C_6$-$C_{20}$ aryl, halo$C_1$-$C_{10}$ alkyl, and halo$C_6$-$C_{20}$ aryl; and $R^1$ and $R^2$ or $R^3$ and $R^2$ may be linked by $C_3$-$C_{10}$ alkylene, $C_3$-$C_{10}$ alkenylene, $C_6$-$C_{20}$ arylene, $C_3$-$C_{10}$ heteroalkylene, $C_3$-$C_{10}$ heteroalkenylene, or $C_6$-$C_{20}$ heteroarylene to form a ring.

More preferably, in the chromium catalyst precursor according to an exemplary embodiment, $M^1$ may be boron (B); L may be acetylacetonate (ACAC); R may be $C_1$-$C_{10}$ alkoxy; W may be acetonitrile (ACN), tetrahydrofuran (THF), diethyl ether, or water ($H_2O$); m may be an integer of 2 to 4; and x may be an integer of 1 to 6.

More preferably, in the chromium catalyst precursor according to an exemplary embodiment, $M^1$ may be aluminum (Al); L may be acetylacetonate (ACAC); R may be a halogen; W may be acetonitrile (ACN), tetrahydrofuran (THF), diethyl ether, or water ($H_2O$); m may be an integer of 2 to 4; and x may be an integer of 1 to 6.

In addition, the present invention provides an ethylene oligomerization catalyst including the chromium catalyst precursor represented by Chemical Formula 1 and a heteroatom ligand.

The ethylene oligomerization catalyst according to an exemplary embodiment has a structure including the chromium catalyst precursor of Chemical Formula 1 and a heteroatom ligand, and specifically, may be represented by $CrM^1(L)_x(R)_{6-x}(L')(W)_m$, wherein $M^1$ is a Group 13 element; L is a ligand in a β-keto enolate form; R is a halogen, $C_1$-$C_{10}$ alkoxy, or $C_6$-$C_{20}$ aryloxy; L' is a heteroatom ligand; W is a neutral coordination ligand; and m is an integer of 0 to 4.

The chromium catalyst precursor of Chemical Formula 1 may be a reaction product of a chromium (III) precursor represented by $Cr(L)_3$ and a Lewis acid containing a Group 13 element represented by $M1(R)_3$, and the reaction thereof may be performed in an inert solvent. That is, the chromium catalyst precursor may be prepared from easily available low-cost raw materials and be present in a homogeneous solution phase. The inert solvent may be, specifically, a nitrile solvent having 2 to 30 carbon atoms, a cyclic or acyclic ether solvent having 2 to 30 carbon atoms, or water ($H_2O$), or a hydrocarbon solvent containing water. More specifically, it may be acetonitrile (ACN), tetrahydrofuran (THF), diethyl ether, or water ($H_2O$), or chlorobenzene, toluene, or the like containing a small amount of water.

Specifically, the chromium catalyst precursor is a product obtained by reacting a chromium (III) precursor and a Lewis acid containing a Group 13 element at the same equivalent ratio in an inert solvent, and may be present in a homogeneous solution phase. A heteroatom ligand having various structures is mixed therewith without a separate separation and purification process, thereby obtaining the ethylene oligomerization catalyst according to an exemplary embodiment. The obtained ethylene oligomerization catalyst is mixed as it is with a cocatalyst without a separate separation and purification process, and may be applied to an ethylene oligomerization reaction in-situ.

The ethylene oligomerization catalyst according to an exemplary embodiment may be prepared, specifically, by reacting the chromium catalyst precursor of Chemical Formula 1 and a heteroatom ligand having various structures. The heteroatom ligand may be an organic compound which may have two atoms which may be coordinated to chromium, for example, two atoms selected from phosphorus (P), arsenic (As), antimony (Sb), oxygen (O), bismuth (Bi), sulfur (S), selenium (Se), nitrogen (N), and the like.

In the ethylene oligomerization catalyst according to an exemplary embodiment, the heteroatom ligand may be a phosphine ligand represented by the following Chemical Formula 3 containing two phosphorus (P) atoms:

$(R^{12})(R^{11})P-Y-Z$      [Chemical Formula 3]

wherein $R^{11}$ and $R^{12}$ are independently of each other hydrocarbyl, heterohydrocarbyl, substituted hydrocarbyl, or substituted heterohydrocarbyl;

Y is a linking group between P and Z;

Z is $*-P(R^{13})(R^{14})$ or

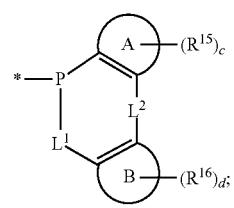

ring A and ring B are independently of each other an aromatic ring;

$L^1$ and $L^2$ are independently of each other a single bond, a heteroatom, a substituted heteroatom, $-C(=O)-$, or $-CR'R''-$;

R' and R" are independently of each other hydrogen, hydrocarbyl, substituted hydrocarbyl, heterohydrocarbyl, or substituted heterohydrocarbyl;

$R^{13}$ to $R^{16}$ are independently of one another hydrocarbyl, heterohydrocarbyl, substituted hydrocarbyl, or substituted heterohydrocarbyl; and c and d are independently of each other an integer of 0 to 4.

An ethylene oligomerization catalyst formed of the chromium catalyst precursor of Chemical Formula 1 and the phosphine ligand of Chemical Formula 3 may implement high activity and high selectivity (selectivity to 1-hexene and 1-octene) which are better when applied to a selective oligomerization reaction.

In the ethylene oligomerization catalyst according to an exemplary embodiment, the heteroatom ligand may be represented by Chemical Formula 3 wherein Y is hydrocarbylene, $-N(R^{21})-$, $-N(R^{21})-N(R^{22})-$, $=C(R^{23})-N(R^{21})-$, $-N(R^{21})-C(R^{23})(R^{24})-$, or $-N(R^{21})-L^3-N(R^{22})-$; $R^{21}$ to $R^{24}$ are independently hydrogen, hydrocarbyl, substituted hydrocarbyl, heterohydrocarbyl, substituted heterohydrocarbyl, or a substituted heteroatom; and $L^3$ is hydrocarbylene.

Preferably, in Chemical Formula 3, Y may be $-N(R^{21})-$, and $R^{21}$ may be hydrocarbyl, substituted hydrocarbyl, heterohydrocarbyl, substituted heterohydrocarbyl, or substituted heteroatom.

In the ethylene oligomerization catalyst according to an exemplary embodiment, the heteroatom ligand of Chemical Formula 3 may be, preferably, a heteroatom ligand having a P—N—P skeletal structure represented by the following Chemical Formula 4 or 5:

[Chemical Formula 4]

$$(R^{12})(R^{11})P-N(R^{21})-P(R^{13})(R^{14})$$

[Chemical Formula 5]

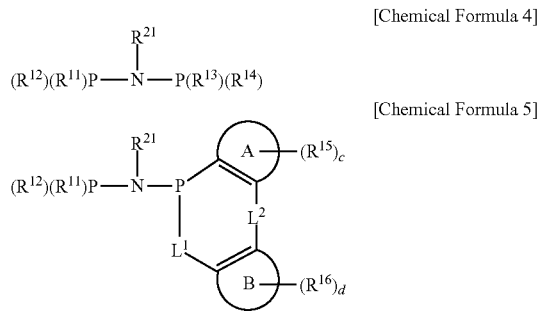

wherein ring A and ring B are independently of each other a $C_6$-$C_{20}$ aromatic ring;

$R^{11}$ to $R^{14}$, $R^{15}$, and $R^{16}$ are independently of each other $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_1$-$C_{10}$ alkyl, $C_2$-$C_{10}$ alkenyl, $C_2$-$C_{10}$ alkynyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, $C_3$-$C_{10}$ cycloalkyl, mercapto$C_1$-$C_{10}$ alkyl, mercapto$C_2$-$C_{10}$ alkenyl, mercapto$C_2$-$C_{10}$ alkynyl, $C_3$-$C_{20}$ heteroaryl, 5-membered to 7-membered heterocycloalkyl, $-NR^{a1}R^{b1}$ or $-SiR^{c1}R^{d1}R^{e1}$;

$R^{a1}$ and $R^{b1}$ are independently of each other hydrogen, $C_1$-$C_{10}$ alkyl, $C_2$-$C_{10}$ alkenyl, $C_2$-$C_{10}$ alkynyl, $C_6$-$C_{20}$ aryl, $C_1$-$C_{10}$ alkylamino, $C_2$-$C_{10}$ alkenylamino, or $C_2$-$C_{10}$ alkynylamino;

$R^{c1}$ is $C_1$-$C_{10}$ alkyl, $C_2$-$C_{10}$ alkenyl, $C_2$-$C_{10}$ alkynyl, or $C_6$-$C_{20}$ aryl;

$R^{d1}$ and $R^{e1}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;

$R^{21}$ is $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_3$-$C_{10}$ cycloalkyl, $C_3$-$C_{20}$ heteroaryl, 5-membered to 7-membered heterocycloalkyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, $-NR^{a2}R^{b2}$, or $-SiR^{c2}R^{d2}R^{e2}$;

$L^1$ and $L^2$ are independently of each other a single bond, $-O-$, $-S-$, $-NR'-$, $-P(=O)R'-$, $-P(=Se)R'-$, $-P(=S)R'-$, $-SiR'R''-$, $-CR'R''-$, or $-C(=O)-$;

R' and R'' are independently of each other hydrogen, $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_3$-$C_{10}$ cycloalkyl, $C_3$-$C_{20}$ heteroaryl, 5-membered to 7-membered heterocycloalkyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, $-NR^{a3}R^{b3}$, or $-SiR^{c3}R^{d3}R^{e3}$;

$R^{a2}$, $R^{b2}$, $R^{a3}$, and $R^{b3}$ are independently of one another hydrogen, $C_1$-$C_{10}$ alkyl, $C_2$-$C_{10}$ alkenyl, $C_2$-$C_{10}$ alkynyl, or $C_6$-$C_{20}$ aryl;

$R^{c2}$ and $R^{c3}$ are independently of each other $C_1$-$C_{10}$ alkyl, $C_2$-$C_{10}$ alkenyl, $C_2$-$C_{10}$ alkynyl, or $C_6$-$C_{20}$ aryl;

$R^{d2}$, $R^{e2}$, $R^{d3}$, and $R^{e3}$ are independently of one another hydrogen, $C_1$-$C_{10}$ alkyl, $C_2$-$C_{10}$ alkenyl, $C_2$-$C_{10}$ alkynyl, or $C_6$-$C_{20}$ aryl;

c and d are independently of each other an integer of 0 to 4; and the aryl, the arylalkyl, the alkyl, the arylalkenyl, the alkenyl, the arylalkynyl, the alkynyl, the alkoxy, the aryloxy, the cycloalkyl, the heteroaryl, or the heterocycloalkyl of $R^{11}$ to $R^{14}$, $R^{15}$, and $R^{16}$, and the alkyl, the alkenyl, the aryl, the aralkyl, the aralkenyl, the aralkynyl, the cycloalkyl, the heteroaryl, the heterocycloalkyl, the alkoxy, the aryloxy, the alkoxycarbonyl, the alkylcarbonyloxy, the alkenylcarbonyloxy, the alkynylcarbonyloxy, the aminocarbonyl, the alkylcarbonylamino, the alkenylcarbonylamino, or the alkynylcarbonylamino of $R^{21}$, R', and R'' may be further substituted by one or more selected from the group consisting of halogens, $C_1$-$C_{10}$ alkyl, halo$C_1$-$C_{10}$ alkyl, $C_2$-$C_{10}$ alkenyl, $C_2$-$C_{10}$ alkynyl, $C_1$-$C_{10}$ alkoxy, halo$C_1$-$C_{10}$ alkoxy, $C_6$-$C_{20}$ aryl, $C_6$-$C_{20}$ aryloxy, 5-membered to 7-membered heterocycloalkyl, $-NR^{a4}R^{b4}$, and $-SiR^{c4}R^{d4}R^{e4}$; and $R^{a4}$ and $R^{b4}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl, and $R^{c4}$ to $R^{e4}$ are independently of each other $C_1$-$C_{10}$ alkyl or $C_1$-$C_{10}$ alkoxy.

In the ethylene oligomerization catalyst according to an exemplary embodiment, the heteroatom ligand may be represented by Chemical Formulae 3 to 5 wherein $L^1$ and $L^2$ are independently of each other a single bond or $-O-$.

Specifically, in Chemical Formulae 4 and 5, ring A and ring B may be independently of each other a $C_6$-$C_{20}$ aromatic ring; $R^{11}$ to $R^{14}$, $R^{15}$, and $R^{16}$ may be independently of each other $C_6$-$C_{20}$ aryl, $C_6$-$C_{20}$ aryl$C_1$-$C_{10}$ alkyl, $C_1$-$C_{10}$ alkyl, $C_2$-$C_{10}$ alkenyl, $C_2$-$C_{10}$ alkynyl, $C_1$-$C_{10}$ alkoxy, $C_6$-$C_{20}$ aryloxy, $C_3$-$C_{10}$ cycloalkyl, mercapto$C_1$-$C_{10}$ alkyl, $C_3$-$C_{20}$ heteroaryl, 5-membered to 7-membered heterocycloalkyl, —NR$^{a1}$R$^{b1}$, or —SiR$^{c1}$R$^{d1}$R$^{e1}$; R$^{a1}$ and R$^{b1}$ may be independently of each other hydrogen, $C_1$-$C_{10}$ alkyl, $C_6$-$C_{20}$ aryl, or $C_1$-$C_{10}$ alkylamino; R$^{c1}$, R$^{d1}$, and R$^{e1}$ may be independently of one another $C_1$-$C_{10}$ alkyl or $C_6$-$C_{20}$ aryl; R$^{21}$ may be $C_1$-$C_{10}$ alkyl, $C_2$-$C_{10}$ alkenyl, $C_2$-$C_{10}$ alkynyl, $C_6$-$C_2$H aryl, $C_6$-$C_{20}$ aryl$C_1$-$C_{10}$ alkyl, $C_3$-$C_{10}$ cycloalkyl, $C_3$-$C_{20}$ heteroaryl, 5-membered to 7-membered heterocycloalkyl, $C_1$-$C_{10}$ alkoxy, $C_6$-$C_{20}$ aryloxy, —NR$^{a2}$R$^{b2}$ or —SiR$^{c2}$R$^{d2}$R$^{e2}$; R$^{a2}$ and R$^{b2}$ may be independently of each other hydrogen or $C_1$-$C_{10}$ alkyl; R$^{e2}$ may be $C_1$-$C_{10}$ alkyl or $C_6$-$C_{20}$ aryl; R$^{d2}$ and R$^{e2}$ may be independently of each other hydrogen, $C_1$-$C_{10}$ alkyl, or $C_6$-$C_{20}$ aryl; L$^1$ and L$^2$ may be independently of each other a single bond or —O—; c and d may be independently of each other an integer of 0 to 4; the aryl, the arylalkyl, the alkyl, the alkenyl, the alkynyl, the alkoxy, the aryloxy, the cycloalkyl, the heteroaryl, or the heterocycloalkyl of R$^{11}$ to R$^{14}$, R$^{15}$, and R$^{16}$, and the alkyl, the alkenyl, the alkynyl, the aryl, the arylalkyl, the cycloalkyl, the heteroaryl, the heterocycloalkyl, the alkoxy, or the aryloxy of R$^{21}$ may be further substituted by one or more selected from the group consisting of halogens, $C_1$-$C_{10}$ alkyl, halo$C_1$-$C_{10}$ alkyl, $C_2$-$C_{10}$ alkenyl, $C_2$-$C_{10}$ alkynyl, $C_1$-$C_{10}$ alkoxy, halo$C_1$-$C_{10}$ alkoxy, $C_6$-$C_{20}$ aryl, $C_6$-$C_{20}$ aryloxy, 5-membered to 7-membered heterocycloalkyl, —NR$^{a4}$R$^{b4}$, and —SiR$^{c4}$R$^{d4}$R$^{e4}$; and R$^{a4}$ and R$^{b4}$ may be independently of each other hydrogen, $C_1$-$C_{10}$ alkyl, or $C_6$-$C_{20}$ aryl, and R$^{c4}$ to R$^{e4}$ may be independently of each other $C_1$-$C_{10}$ alkyl or $C_1$-$C_{10}$ alkoxy.

Preferably, in Chemical Formulae 4 and 5 according to an exemplary embodiment, ring A and ring B may be independently of each other $C_6$-$C_{20}$ aromatic ring; R$^{11}$ to R$^{14}$ may be independently of one another $C_6$-$C_{20}$ aryl, $C_6$-$C_{20}$ aryl$C_1$-$C_{10}$ alkyl, $C_3$-$C_{10}$ cycloalkyl, or $C_3$-$C_{20}$ heteroaryl; R$^{15}$ and R$^{16}$ may be independently of each other $C_6$-$C_{20}$ aryl, $C_6$-$C_{20}$ aryl$C_1$-$C_{10}$ alkyl, $C_1$-$C_{10}$ alkyl, $C_2$-$C_{10}$ alkenyl, $C_2$-$C_{10}$ alkynyl, $C_3$-$C_{10}$ cycloalkyl, mercapto$C_1$-$C_{10}$ alkyl, $C_3$-$C_{20}$ heteroaryl, or 5-membered to 7-membered heterocycloalkyl; R$^{21}$ may be $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, or $C_3$-$C_{10}$ cycloalkyl; L$^1$ and L$^2$ may be independently of each other a single bond or —O—; c and d may be independently of each other an integer of 0 to 4; and the aryl, the arylalkyl, the alkyl, the cycloalkyl, or the heteroaryl of R$^{11}$ to R$^{14}$, the aryl, the arylalkyl, the alkyl, the alkenyl, the alkynyl, the cycloalkyl, the heteroaryl, or the heterocycloalkyl of R$^{15}$ and R$^{16}$, and the alkyl, the alkenyl, the alkynyl, the aryl, the arylalkyl, or the cycloalkyl of R$^{21}$ may be further substituted by one or more selected from the group consisting of halogens, $C_1$-$C_{10}$ alkyl, halo$C_1$-$C_{10}$ alkyl, $C_1$-$C_{10}$ alkoxy, halo$C_1$-$C_{10}$ alkoxy, $C_6$-$C_{20}$ aryl, $C_6$-$C_{20}$ aryloxy, 5-membered to 7-membered heterocycloalkyl, amino, mono- or di$C_1$-$C_{10}$ alkylamino, tri$C_1$-$C_{10}$ alkylsilyl, di$C_1$-$C_{10}$ alkylarylsilyl, $C_1$-$C_{10}$ alkyldi$C_6$-$C_{20}$ arylsilyl, tri$C_1$-$C_{10}$ alkoxysilyl, and tri$C_6$-$C_{20}$ arylsilyl.

More preferably, in Chemical Formulae 4 and 5 according to an exemplary embodiment, ring A and ring B may be independently of each other a $C_6$-$C_{20}$ aromatic ring; R$^{11}$ to R$^{14}$ may be independently of each other $C_6$-$C_{20}$ aryl; R$^{15}$ and R$^{16}$ may be independently of each other $C_1$-$C_{10}$ alkyl; R$^{21}$ may be $C_1$-$C_{10}$ alkyl or $C_3$-$C_{10}$ cycloalkyl; L$^1$ and L$^2$ may be independently of each other a single bond or —O—; c and d may be independently of each other an integer of 0 or 1; and the aryl of R$^{11}$ to R$^{14}$ may be further substituted by one or more selected from the group consisting of halogens, $C_1$-$C_{10}$ alkyl, halo$C_1$-$C_{10}$ alkyl, $C_1$-$C_{10}$ alkoxy, halo$C_1$-$C_{10}$ alkoxy, $C_6$-$C_{20}$ aryl, $C_6$-$C_{20}$ aryloxy, 5-membered to 7-membered heterocycloalkyl, tri$C_1$-$C_{10}$ alkylsilyl, di$C_1$-$C_{10}$ alkylarylsilyl, $C_1$-$C_{10}$ alkyldi$C_6$-$C_{20}$ arylsilyl, tri$C_1$-$C_{10}$ alkoxysilyl, and tri$C_6$-$C_{20}$ arylsilyl.

In a specific example, in Chemical Formula 5, both L$^1$ and L$^2$ may be a single bond.

In a specific example, in Chemical Formula 5, L$^1$ may be a single bond and L$^2$ may be —O—.

In a specific example, in Chemical Formula 5, the ring A and the ring B may be independently of each other benzene or naphthalene.

In the ethylene oligomerization catalyst according to an exemplary embodiment, the heteroatom ligand of Chemical Formula 5 may be, preferably, a heteroatom ligand having a P—N—P skeletal structure represented by the following Chemical Formula 6:

[Chemical Formula 6]

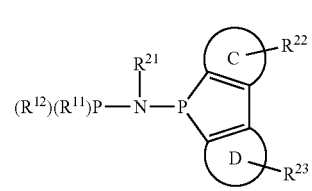

wherein
R$^{11}$ and R$^{12}$ are independently of each other $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_1$-$C_{10}$ alkyl, $C_2$-$C_{10}$ alkenyl, $C_2$-$C_{10}$ alkynyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, $C_3$-$C_{10}$ cycloalkyl, mercapto$C_1$-$C_{10}$ alkyl, mercapto$C_2$-$C_{10}$ alkenyl, mercapto$C_2$-$C_{10}$ alkynyl, $C_3$-$C_{20}$ heteroaryl, 5-membered to 7-membered heterocycloalkyl, —NR$^{a1}$R$^{b1}$, or —SiR$^{c1}$R$^{d1}$R$^{e1}$;

R$^{a1}$ and R$^{b1}$ are independently of each other hydrogen, $C_1$-$C_{10}$ alkyl, $C_2$-$C_{10}$ alkenyl, $C_2$-$C_{10}$ alkynyl, $C_6$-$C_{20}$ aryl, $C_1$-$C_{10}$ alkylamino, $C_2$-$C_{10}$ alkenylamino, or $C_2$-$C_{10}$ alkynylamino;

R$^{c1}$ is $C_1$-$C_{10}$ alkyl, $C_2$-$C_{10}$ alkenyl, $C_2$-$C_{10}$ alkynyl, or $C_6$-$C_{20}$ aryl;

R$^{d1}$ and R$^{e1}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;

R$^{21}$ is $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_3$-$C_{10}$ cycloalkyl, $C_3$-$C_{20}$ heteroaryl, 5-membered to 7-membered heterocycloalkyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, —NR$^{a2}$R$^{b2}$, or —SiR$^{c2}$R$^{d2}$R$^{e2}$;

R$^{a2}$ and R$^{b2}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;

R$^{c2}$ is $C_1$-$C_{10}$ alkyl, $C_2$-$C_{10}$ alkenyl, $C_2$-$C_{10}$ alkynyl, or $C_6$-$C_{20}$ aryl;

$R^{d2}$ and $R^{e2}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;

ring C and ring D are independently of each other benzene or naphthalene;

$R^{22}$ and $R^{23}$ are hydrogen, $C_1$-$C_{10}$ alkyl, $C_6$-$C_{20}$ aryl, $C_3$-$C_{10}$ cycloalkyl, $C_6$-$C_{20}$ aryl$C_1$-$C_{10}$ alkyl, or $C_1$-$C_{10}$ alkyl$C_6$-$C_{20}$ aryl; and the aryl, the arylalkyl, the alkyl, the arylalkenyl, the alkenyl, the arylalkynyl, the alkynyl, the alkoxy, the aryloxy, the cycloalkyl, the heteroaryl, and the heterocycloalkyl of $R^{11}$ and $R^{12}$, and the alkyl, the alkenyl, the aryl, the aralkyl, the aralkenyl, the aralkynyl, the cycloalkyl, the heteroaryl, the heterocycloalkyl, the alkoxy, the aryloxy, the alkoxycarbonyl, the alkylcarbonyloxy, the alkenylcarbonyloxy, the alkynylcarbonyloxy, the aminocarbonyl, the alkylcarbonylamino, the alkenylcarbonylamino, or the alkynylcarbonylamino of $R^{21}$ may be further substituted by one or more selected from the group consisting of halogens, $C_1$-$C_{10}$ alkyl, halo$C_1$-$C_{10}$ alkyl, $C_2$-$C_{10}$ alkenyl, $C_2$-$C_{10}$ alkynyl, $C_1$-$C_{10}$ alkoxy, halo$C_1$-$C_{10}$ alkoxy, $C_6$-$C_{20}$ aryl, $C_6$-$C_{20}$ aryloxy, 5-membered to 7-membered heterocycloalkyl, —$NR^{a4}R^{b4}$, and —$SiR^{c4}R^{d4}R^{e4}$; and $R^{a4}$ and $R^{b4}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl, and $R^{c4}$ to $R^{e4}$ are independently of each other $C_1$-$C_{10}$ alkyl or $C_1$-$C_{10}$ alkoxy.

In the ethylene oligomerization catalyst according to an exemplary embodiment, the heteroatom ligand of Chemical Formula 6 may be, preferably, a heteroatom ligand having a P—N—P skeletal structure represented by the following Chemical Formula 7 or Formula 8:

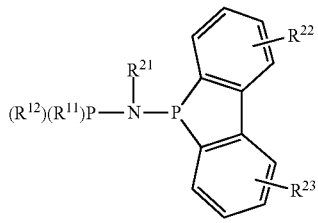

[Chemical Formula 7]

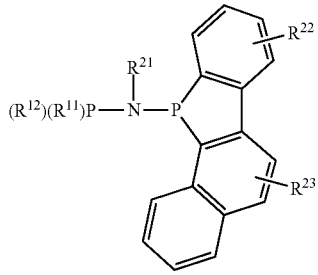

[Chemical Formula 8]

wherein $R^{11}$ and $R^{12}$ are independently of each other $C_6$-$C_{20}$ aryl, $C_6$-$C_{20}$ aryl$C_1$-$C_{10}$ alkyl, $C_1$-$C_{10}$ alkyl, $C_2$-$C_{10}$ alkenyl, $C_2$-$C_{10}$ alkynyl, $C_1$-$C_{10}$ alkoxy, $C_6$-$C_{20}$ aryloxy, $C_3$-$C_{10}$ cycloalkyl, mercapto$C_1$-$C_{10}$ alkyl, $C_3$-$C_{20}$ heteroaryl, 5-membered to 7-membered heterocycloalkyl, —$NR^{a1}R^{b1}$, or —$SiR^{c1}R^{d1}R^{e1}$;

$R^{a1}$ and $R^{b1}$ are independently of each other hydrogen, $C_1$-$C_{10}$ alkyl, $C_6$-$C_{20}$ aryl, or $C_1$-$C_{10}$ alkylamino;

$R^{c1}$, $R^{d1}$, and $R^{e1}$ are independently of one another $C_1$-$C_{10}$ alkyl, or $C_6$-$C_{20}$ aryl;

$R^{21}$ is $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, $C_3$-$C_{10}$ cycloalkyl, $C_3$-$C_{10}$ heteroaryl, 5-membered to 7-membered heterocycloalkyl, $C_1$-$C_{10}$ alkoxy, $C_6$-$C_{20}$ aryloxy, —$NR^{a2}R^{b2}$, or —$SiR^{c2}R^{d2}R^{e2}$;

$R^{a2}$ and $R^{b2}$ are independently of each other hydrogen or $C_1$-$C_{10}$ alkyl;

$R^{c2}$ is $C_1$-$C_{10}$ alkyl or $C_6$-$C_{20}$ aryl;

$R^{d2}$ and $R^{e2}$ are independently of each other hydrogen, $C_1$-$C_{10}$ alkyl, or $C_6$-$C_{20}$ aryl;

$R^{22}$ and $R^{23}$ are hydrogen, $C_1$-$C_{10}$ alkyl, $C_6$-$C_{20}$ aryl, $C_3$-$C_{10}$ cycloalkyl, $C_6$-$C_{20}$ aryl$C_1$-$C_{10}$ alkyl, or $C_1$-$C_{10}$ alkyl$C_6$-$C_{20}$ aryl; and the aryl, the arylalkyl, the alkyl, the alkenyl, the alkynyl, the alkoxy, the aryloxy, the cycloalkyl, the heteroaryl, or the heterocycloalkyl of $R^{11}$ and $R^{12}$, and the alkyl, the alkenyl, the alkynyl, the aryl, the arylalkyl, the cycloalkyl, the heteroaryl, the heterocycloalkyl, the alkoxy, or the aryloxy of $R^{21}$ may be further substituted by one or more selected from the group consisting of halogens, $C_1$-$C_{10}$ alkyl, halo$C_1$-$C_{10}$ alkyl, $C_2$-$C_{10}$ alkenyl, $C_2$-$C_{10}$ alkynyl, $C_1$-$C_{10}$ alkoxy, halo$C_1$-$C_{10}$ alkoxy, $C_6$-$C_{20}$ aryl, $C_6$-$C_{20}$ aryloxy, 5-membered to 7-membered heterocycloalkyl, —$NR^{a4}R^{b4}$, and —$SiR^{c4}R^{d4}R^{e4}$; and $R^{a4}$ and $R^{b4}$ are independently of each other hydrogen, $C_1$-$C_{10}$ alkyl, or $C_6$-$C_{20}$ aryl, and $R^{c4}$ to $R^{e4}$ are independently of each other $C_1$-$C_{10}$ alkyl or $C_1$-$C_{10}$ alkoxy.

Preferably, in Chemical Formulae 7 and 8 according to an exemplary embodiment, $R^{11}$ and $R^{12}$ may be independently of each other $C_6$-$C_{20}$ aryl, $C_6$-$C_{20}$ aryl$C_1$-$C_{10}$ alkyl, $C_3$-$C_{10}$ cycloalkyl, or $C_3$-$C_{20}$ heteroaryl; $R^{21}$ may be $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, or $C_3$-$C_{10}$ cycloalkyl; $R^{22}$ and $R^{23}$ are hydrogen, $C_1$-$C_{10}$ alkyl, $C_6$-$C_{20}$ aryl, $C_3$-$C_{10}$ cycloalkyl, $C_6$-$C_{20}$ aryl$C_1$-$C_{10}$ alkyl, or $C_1$-$C_{10}$ alkyl$C_6$-$C_{20}$ aryl; and the aryl, the arylalkyl, the alkyl, the cycloalkyl, or the heteroaryl of $R^{11}$ and $R^{12}$, and the alkyl, the alkenyl, the alkynyl, the aryl, the arylalkyl, or the cycloalkyl of $R^{21}$ may be further substituted by one or more selected from the group consisting of halogens, $C_1$-$C_{10}$ alkyl, halo$C_1$-$C_{10}$ alkyl, $C_1$-$C_{10}$ alkoxy, halo$C_1$-$C_{10}$ alkoxy, $C_6$-$C_{20}$ aryl, $C_6$-$C_{20}$ aryloxy, 5-membered to 7-membered heterocycloalkyl, amino, mono- or di$C_1$-$C_{10}$ alkylamino, tri$C_1$-$C_{10}$ alkylsilyl, di$C_1$-$C_{10}$ alkylarylsilyl, $C_1$-$C_{10}$ alkyl diC6-C20arylsilyl, tri$C_1$-$C_{10}$ alkoxysilyl, and tri$C_6$-$C_{20}$ arylsilyl.

More preferably, in Chemical Formulae 7 and 8 according to an exemplary embodiment, $R^{11}$ and $R^{12}$ may be independently of each other $C_6$-$C_{20}$ aryl; $R^{21}$ is $C_1$-$C_{10}$ alkyl or $C_3$-$C_{10}$ cycloalkyl; $R^{22}$ and $R^{23}$ are hydrogen or $C_1$-$C_{10}$ alkyl; the aryl of $R^{11}$ and $R^{12}$ may be further substituted from the group consisting of halogen, $C_1$-$C_{10}$ alkyl, halo$C_1$-$C_{10}$ alkyl, $C_1$-$C_{10}$ alkoxy, halo$C_1$-$C_{10}$ alkoxy, $C_6$-$C_{20}$ aryl, $C_6$-$C_{20}$ aryloxy, 5-membered to 7-membered heterocycloalkyl, tri$C_1$-$C_{10}$ alkylsilyl, di$C_1$-$C_{10}$ alkylarylsilyl, $C_1$-$C_{10}$ alkyldi$C_6$-$C_{20}$ arylsilyl, tri$C_1$-$C_{10}$ alkoxysilyl, and tri$C_6$-$C_{20}$ arylsilyl.

In a more preferred aspect of having more improved catalytic activity and ethylene oligomer selectivity, in Chemical Formulae 7 and 8 according to an exemplary embodiment, $R^{11}$ and $R^{12}$ may be independently of each other $C_6$-$C_{20}$ aryl substituted with tri$C_1$-$C_{10}$ alkylsilyl.

In the ethylene oligomerization catalyst according to an exemplary embodiment, the chromium catalyst precursor may be represented by Chemical Formula 1 in which $M^1$ is boron (B) or aluminum (Al); R is a halogen or $C_1$-$C_{10}$ alkoxy; W is acetonitrile (ACN), tetrahydrofuran (THF), diethyl ether, or water ($H_2O$); m is an integer of 2 to 4; x is an integer of 1 to 6; and L is an acac-based ligand having the following structure:

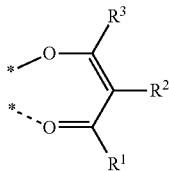

wherein $R^1$ and $R^3$ are independently of each other $C_1$-$C_{10}$ alkyl or $C_6$-$C_{20}$ aryl, and the alkyl and the aryl of $R^1$ and $R^3$ may be further substituted by one or more substituents selected from halogens, $C_1$-$C_{10}$ alkyl, $C_6$-$C_{20}$ aryl, halo$C_1$-$C_{10}$ alkyl, and halo$C_6$-$C_{20}$ aryl;

$R^2$ is hydrogen, a halogen, $C_1$-$C_{10}$ alkyl, or $C_6$-$C_{20}$ aryl, and the alkyl and the aryl of $R^2$ may be further substituted by one or more selected from halogens, $C_1$-$C_{10}$ alkyl, $C_6$-$C_{20}$ aryl, halo$C_1$-$C_{10}$ alkyl, and halo$C_6$-$C_{20}$ aryl; and $R^1$ and $R^2$ or $R^3$ and $R^2$ may be linked by $C_3$-$C_{10}$ alkylene, $C_3$-$C_{10}$alkenylene, $C_6$-$C_{20}$ arylene, $C_3$-$C_{10}$ heteroalkylene, $C_3$-$C_{10}$ heteroalkenylene, or $C_6$-$C_{20}$ heteroarylene to form a ring.

The ethylene oligomerization catalyst according to an exemplary embodiment is formed by including a chromium catalyst precursor prepared in a homogeneous solution phase from low-cost raw materials such as a chromium (III) precursor and a Lewis acid containing a Group 13 element, and a heteroatom ligand, and may produce 1-hexene and 1-octene in a high yield with high activity and high selectivity while maintaining the activity of the reaction stably, by oligomerizing ethylene in-situ with an organoboron compound-based cocatalyst without the use of an aluminoxane cocatalyst such as methylaluminoxane (MAO).

Specifically, the ethylene oligomerization catalyst is a product obtained by reacting the chromium (III) precursor and a Lewis acid containing a Group 13 element at the same equivalent ratio in an inert solvent, and may be prepared by mixing and reacting a chromium catalyst precursor which may be present in a homogeneous solution phase with a heteroatom ligand having various structures without a separate separation and purification process. The ethylene oligomerization catalyst prepared is also mixed as it is with an organoboron compound-based cocatalyst without a separate separation and purification process, and may be applied to an ethylene oligomerization reaction in-situ.

Since the ethylene oligomerization catalyst according to an exemplary embodiment has excellent catalytic activity, may implement excellent selectivity to 1-hexene and 1-octene, may significantly suppress production of a polymer such as polyethylene, and does not cause tube blockage or fouling in the ethylene oligomerization process, it is very economical and efficient.

In addition, the present invention provides a method of producing an ethylene oligomer including: bringing a catalyst system including the ethylene oligomerization catalyst and an organoboron compound-based cocatalyst into contact with an ethylene monomer to produce an ethylene oligomer.

The method of preparing an ethylene oligomer according to an exemplary embodiment is characterized by not using high-cost alkylaluminoxane such as methylaluminoxane (MAO) or modified-methylaluminoxane (MMAO) which is conventionally used as a cocatalyst, in order to prepare 1-hexene or 1-octene with high activity and high selectivity from ethylene.

In the preparation method according to an exemplary embodiment, the catalyst system may include the ethylene oligomerization catalyst and an organoboron compound-based cocatalyst, for effective ethylene oligomerization.

The ethylene oligomerization catalyst may include the chromium catalyst precursor of Chemical Formula 1 and a heteroatom ligand. Specifically, the ethylene oligomerization catalyst is a product obtained by reacting the chromium (III) precursor and a Lewis acid containing a Group 13 element at the same equivalent ratio in an inert solvent, and may be prepared by mixing and reacting a chromium catalyst precursor which may be present in a homogeneous solution phase with a heteroatom ligand having various structures without a separate separation and purification process. The ethylene oligomerization catalyst prepared is also mixed as it is with an organoboron compound-based cocatalyst without a separate separation and purification process, and may be applied to an ethylene oligomerization reaction in-situ.

In the preparation method according to an exemplary embodiment, the catalyst system includes an organoboron compound-based cocatalyst as a cocatalyst which activates the oligomerization catalyst.

The organoboron compound-based cocatalyst according to an exemplary embodiment may be an organoboron compound represented by the following Chemical Formula 9:

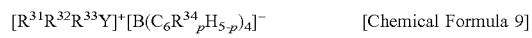

[Chemical Formula 9]

wherein

Y is C or NH;

$R^{31}$ to $R^{33}$ are independently of one another hydrogen, $C_1$-$C_{20}$ alkyl, or $C_6$-$C_{20}$ aryl, and the alkyl or the aryl of $R^{31}$ may be further substituted by one or more selected from the group consisting of $C_1$-$C_{20}$ alkyl and $C_6$-$C_{20}$ aryl;

$R^{34}$ is fluoro, $C_1$-$C_{20}$ alkyl, or $C_1$-$C_{20}$ alkoxy, and the alkyl or the alkoxy of $R^{34}$ may be further substituted by one or more fluoro(s); and p is an integer of 3 to 5.

In an exemplary embodiment, in Chemical Formula 9, Y may be C.

A specific example of the organoboron compound includes trityl tetrakis(pentafluorophenyl)borate, trityl tetrakis(trifluoromethylphenyl)borate, trityl tetrakis(3,5-bis(trifluoromethyl)phenyl)borate, trimethylammonium tetrakis(trifluoromethylphenyl)borate, triethylammonium tetrakis (pentafluorophenyl)borate, tripropylammonium tetrakis (pentafluorophenyl)borate, tributylammonium tetrakis (trifluoromethylphenyl)borate, tributylammonium tetrakis (pentafluorophenyl)borate, tributylammonium tetrakis(3,5-bis(trifluoromethyl)phenyl)borate, N,N-dimethylanilinium tetrakis(pentafluorophenyl)borate, N,N-diethylanilinium tetrakis(pentafluorophenyl)borate, N,N-dimethylanilinium tetrakis(3,5-bis(trifluoromethyl)phenyl)borate, methyldiphenylammonium tetrakis(pentafluorophenyl)borate, ethyldiphenylammonium tetrakis(pentafluorophenyl)borate, and the like, which may be used alone or in combination of two or more, and preferably, at least one or more selected from trityl tetrakis(pentafluorophenyl)borate, trityl tetrakis (trifluoromethylphenyl)borate, and trityl tetrakis(3,5-bis(trifluoromethyl)phenyl)borate may be used.

In the preparation method according to an exemplary embodiment, the catalyst system may further include an alkylaluminum compound represented by the following Chemical Formula 10:

AlR$^{41}$R$^{42}$R$^{43}$  [Chemical Formula 10]

wherein

R$_{41}$ is C$_1$-C$_{20}$ alkyl; and

R$^{42}$ and R$^{43}$ are independently of each other C$_1$-C$_{20}$ alkyl or a halogen.

Preferably, in Chemical Formula 10, R$^{41}$, R$^{42}$, and R$^{43}$ may be independently of one another C$_1$-C$_{10}$ alkyl, and more preferably, R$^{41}$, R$^{42}$, and R$^{43}$ may be independently of one another C$_1$-C$_6$ alkyl.

A specific example of the alkylaluminum includes trimethylaluminum (TMA), triethylaluminum (TEAL), tripropylaluminum, triisobutylaluminum (TIBA), trihexylaluminum, tri-n-octylaluminum, methylaluminum dichloride, ethylaluminum dichloride, propylaluminum dichloride, isobutylaluminum dichloride, hexylaluminum dichloride, dimethylaluminum chloride, diethylaluminum chloride, dipropylaluminum chloride, diisobutylaluminum chloride, dihexylaluminum chloride, and the like, which may be used alone or in combination of two or more, and preferably, at least one or more selected from triethylaluminum (TEAL), triisobutylaluminum (TIBA), trihexylaluminum, and tri-n-octylaluminum may be used.

When the organoboron compound of Chemical Formula 9 and the alkylaluminum compound of Chemical Formula 10 are used in combination, the efficiency of the ethylene oligomerization reaction may be further increased.

In the method of preparing an ethylene oligomer according to an exemplary embodiment, a ratio between the ethylene oligomerization catalyst and the organoboron compound-based cocatalyst is 1:1 to 1,000, preferably 1:1 to 500, and more preferably 1:1 to 100, based on the mole ratio of a chromium (Cr) atom:boron (B) atom. Within the range, ethylene oligomerization activity may be maintained excellent.

In the method of preparing an ethylene oligomer according to an exemplary embodiment, a ratio among the ethylene oligomerization catalyst, the organoboron compound-based cocatalyst, and the alkylaluminum compound is 1:1 to 1,000:100 to 10,000, preferably 1:1 to 500:100 to 5,000, and more preferably 1:1 to 100:500 to 5,000, based on the mole ratio of a chromium (Cr) atom:boron (B) atom:aluminum (Al) atom. Within the range, ethylene oligomerization activity may be maintained better.

The catalyst system may further include other possible components in addition to the ethylene oligomerization catalyst and the organoboron compound-based cocatalyst, as long as the components do not impair the nature of the present invention.

In the preparation method according to an exemplary embodiment, the catalyst system may be prepared by adding the organoboron compound-based cocatalyst to the ethylene oligomerization catalyst present in a homogeneous solution phase. Here, the catalyst system may further include an inert solvent. The inert solvent may be the same as a polymerization solvent described later. Mixing of the ethylene oligomerization catalyst and the organoboron compound-based cocatalyst may be performed at a temperature of 20 to 250° C., and while the catalyst components are mixed, the presence of olefin may generally represent a protection effect to provide improved catalyst performance. A more preferred temperature range is 20 to 100° C.

In the preparation method according to an exemplary embodiment, the ethylene oligomerization product is an ethylene oligomer, in particular, 1-hexene or 1-octene, and may be prepared by a homogeneous liquid phase reaction or a two-phase liquid/liquid reaction in the presence of an inert solvent, or a bulk phase reaction or a gas phase reaction in which a product olefin acts as a main medium, using the catalyst system according to the present invention and common device and contact technology, but a homogeneous liquid phase reaction in the presence of an inert solvent is preferred.

In the preparation method according to an exemplary embodiment, the ethylene oligomerization reaction may be performed in an inert solvent and any inert solvent which does not react with the ethylene oligomerization catalyst of the present invention and the organoboron compound-based cocatalyst. In terms of improving catalyst solubility and catalytic activity, the inert solvent may be a hydrocarbon-based solvent, and specifically, may be an aliphatic or aromatic hydrocarbon solvent which is unsubstituted or substituted with a halogen.

Specifically, the hydrocarbon solvent may be C$_4$-C$_{20}$ an aliphatic hydrocarbon solvent unsubstituted or substituted with a halogen, a C$_6$-C$_{20}$ aromatic hydrocarbon solvent unsubstituted or substituted with a halogen, a mixture thereof, and the like. More specifically, it may be, for example, hexane, heptane, octane, nonene, decane, undecane, dodecane, tetradecane, dimethylpentane, trimethylpentane, methylhexane, dimethylhexane, methylheptane, dichloromethane, cyclohexane, methylcyclohexane (MCH), ethylcyclohexane, isopropylcyclohexane, dimethylcyclohexane, trimethylcyclohexane, benzene, toluene, xylene, mesitylene, ethylenebenzene, cumene, chlorobenzene (CB), dichlorobenzene, fluorobenzene, and the like, preferably hexane, heptane, cyclohexane, methylcyclohexane (MCH), toluene, chlorobenzene (CB), or a combination thereof. When the hydrocarbon solvent exemplified above is used, it is easier to separate 1-hexene and 1-octene which are products with a solvent after the oligomerization reaction, and the activity may be high.

In the preparation method according to an exemplary embodiment, the ethylene oligomerization reaction may be performed at a temperature of 20 to 250° C., preferably 20 to 160° C., and more preferably 60 to 160° C., under a reaction pressure of an atmospheric pressure to 100 bar, preferably 10 to 70 bar.

In the preparation method according to an exemplary embodiment, the ethylene oligomer may be 1-hexene, 1-octene, or a mixture thereof.

In the preparation method according to an exemplary embodiment, 1-octene may be obtained at 90 wt % or more, preferably 95% or more, and more preferably 99 wt % or more, with respect to the total weight of a C8 product formed from ethylene by the ethylene oligomerization reaction. In this case, the yield refers to the wt % of 1-octene formed with respect to the total weight of the C8 product formed.

In the preparation method according to an exemplary embodiment, 1-hexene may be obtained at 50 wt % or more, preferably 70 wt % or more, and more preferably 90 wt % or more, with respect to the total weight of a C6 product formed from ethylene by the ethylene oligomerization reaction. In this case, the yield refers to the wt % of 1-hexene formed with respect to the total weight of the C6 product formed.

In the preparation method according to an exemplary embodiment, the ethylene oligomerization reaction may be in a plant including any type of reactor. An example of the reactor includes a batch reactor, a semi-bath reactor, and a continuous reactor, but is not limited thereto. The plant may include a reactor, an inlet of an olefin reactor and an oligomerization catalyst system, a line for outflow of an oligomerization reaction product, and at least one separator for separating an oligomerization reaction product, in which the catalyst system may include the ethylene oligomerization catalyst described above and the organoboron compound-based cocatalyst, or the chromium catalyst precursor, the heteroatom ligand, and the organoboron compound-based cocatalyst.

According to the present invention, ethylene is oligomerized in-situ by activation with the organoboron compound-based cocatalyst together with the preparation of the ethylene oligomerization catalyst, thereby improving the activity and the selectivity of the ethylene oligomerization reaction to a significantly excellent level without the use of high-cost alkylaluminoxane such as methylaluminoxane (MAO) or modified methylaluminoxane (MMAO) to prepare 1-hexene and 1-octene in a high yield. In addition, production of polymer by-products such as polyethylene may be further suppressed.

The following Examples specifically describe the effect of the present invention. However, the following Examples are only illustrative of the present invention, and do not limit the scope of the present invention.

Preparation of Ligand

[Preparation Example 1] Preparation of Ligand L1

The entire reaction process was performed while the nitrogen atmosphere was maintained. 10.0 g (23.5 mmol) of 2,2'-dibromo-4,4'-di-tert-butyl-1,1'-biphenyl and 130 mL of diethyl ether were added to a 250 mL round bottom flask (RBF), stirring was performed in an acetone/dry ice bath for 30 minutes, and then 19 mL (47.1 mmol) of n-BuLi was added dropwise for 20 minutes. The reactant was stirred at room temperature for 2 hours, stored for 10 minutes in a liquid $N_2$ bath, and then 22.6 g (164 mmol) of $PCl_3$ was added dropwise using a dropping funnel. The reaction vessel was taken out of the liquid $N_2$ bath, and stirring was performed at room temperature for 1 hour. The solvent of the reactant was dried under vacuum, the reactant was transferred to a glove box, 30 mL of hexane was added thereto, and stirring was performed for 30 minutes. A bright yellow solid produced was filtered, dried, and dried under vacuum at room temperature for 4 hours, 30 mL of acetonitrile was added thereto, and stirring was performed for 6 hours. A produced white solid was filtered, and dried at room temperature for 15 hours. 19.5 g of the produced white powder (3,7-di-tert-butyl-chloro-5H-benzo[b]phosphindole, yield: 83%) was added to a 250 mL RBF in the glove box, 50 mL of hexane was added thereto, stirring was performed at room temperature for 30 minutes, and then 17.8 g (301 mmol) of isopropylamine was added all at once. The reactant was stirred at room temperature for 15 hours to produce a white solid compound, which was removed by filtration, and a filtrate, which was dried under vacuum to obtain 20.0 g of white powder (3,7-di-tert-butyl-N-isopropyl-5H-benzo[b]phosphindol-5-amine, yield: 93%). 0.81 g (2.3 mmol) of 3,7-di-tert-butyl-N-isopropyl-5H-benzo[b]phosphindol-5-amine, 2.30 g (22.6 mmol) of triethylamine, and 16 mL of hexane were added to a 100 mL RBF in the glove box, and then the glove box was stored in a refrigerator (−20° C.) for 30 minutes. 0.57 g (2.3 mmol) of chloro-di-o-tolylphosphine and 14 mL of hexane were added to a 20 mL glass vial, and then the glass vial was stored in a glove box refrigerator (−20° C.) for 30 minutes. The cooled 20 mL glass vial solution was added all at once to a cooled 100 mL RBF, and then stirring was performed for 15 hours. A solid produced in the reactant was removed by filtration, and a filtrate was dried under vacuum. 30 mL of hexane was added to the dried reactant, stirring was performed for 30 minutes, the mixture was added to a neutral alumina column baked at 150° C. and passed through 120 mL of a solution of hexane:diethyl ether=4:1, and the solution was dried under vacuum to obtain 0.64 g of a white solid (ligand L1).

$^1$H NMR (500 MHz), d-benzene, 25° C.: δ=8.27 (br, 2H), 7.79 (br, 3H), 7.65 (d, 3H), 7.33 (d, 3H), 7.13 (br, 3H), 3.09 (m, 1H), 2.51 (br, 6H), 1.32 (br, 9H), 1.05 (br, 6H)

[Preparation Example 2] Preparation of Ligand L2

0.81 g (2.3 mmol) of 3,7-di-tert-butyl-N-isopropyl-5H-benzo[b]phosphindol-5-amine, 2.30 g (22.6 mmol) of triethylamine, and 16 mL of hexane were added to a 100 mL RBF in the glove box, and then the glove box was stored in a refrigerator (−20° C.) for 30 minutes. 0.50 g (2.3 mmol) of chloro-di-o-tolylphosphine and 14 mL of hexane were added to a 20 mL glass vial, and then the glass vial was stored in a glove box refrigerator (−20° C.) for 30 minutes. The cooled 20 mL glass vial solution was added all at once to a cooled 100 mL RBF, and then stirring was performed for 15 hours. A solid produced in the reactant was removed by filtration, and a filtrate was dried under vacuum. 30 mL of hexane was added to the dried reactant, stirring was performed for 30 minutes, the mixture was added to a neutral alumina column baked at 150° C. and passed through 120 mL of a solution of hexane:diethyl ether=4:1, and the solution was dried under vacuum to obtain 0.55 g of a white solid (ligand L2).

$^1$H NMR (500 MHz), d-benzene, 25° C.: δ=8.07 (br, 4H), 7.65 (br, 3H), 7.55 (br, 1H), 7.34 (br, 6H), 7.21 (br, 2H), 2.89 (m, 1H), 1.28 (br, 9H), 1.10 (br, 6H)

[Preparation Example 3] Preparation of Ligand L3

The entire reaction process was performed while the nitrogen atmosphere was maintained. 9.90 g (29.9 mmol) of 3,7-di-tert-butyl-chloro-5H-benzo[b]phosphindol and 50 mL of hexane were added to a 250 mL of glove box, stirring was performed at room temperature for 30 minutes, and then 2.12 g (29.9 mmol) of cyclobutylamine was added thereto all at once. The reactant was stirred at room temperature for 15 hours to produce a white solid compound, which was removed by filtration, and a filtrate, which was dried under vacuum to obtain 10.0 g of white powder (3,7-di-tert-butyl-N-cyclobutyl-5H-benzo[b]phosphindol-5-amine, yield: 91%). 0.84 g (2.3 mmol) of 3,7-di-tert-butyl-N-cyclobutyl-5H-benzo[b]phosphindol-5-amine, 2.30 g (22.6 mmol) of triethylamine, and 16 mL of hexane were added to a 100 mL RBF in the glove box, and then the glove box was stored in a refrigerator (−20° C.) for 30 minutes. 0.57 g (2.3 mmol) of chloro-di-o-tolylphosphine and 14 mL of hexane were added to a 20 mL glass vial, and then the glass vial was stored in a glove box refrigerator (−20° C.) for 30 minutes. The cooled 20 mL glass vial solution was added all at once to a cooled 100 mL RBF, and then stirring was performed for 15 hours. A solid produced in the reactant was removed by filtration, and a filtrate was dried under vacuum. 30 mL of hexane was added to the dried reactant, stirring was performed for 30 minutes, the mixture was added to a neutral alumina column baked at 150° C. and passed through 120 mL of a solution of hexane:diethyl ether=4:1, and the solution was dried under vacuum to obtain 0.85 g of a white solid (ligand L3).

$^1$H NMR (500 MHz), d-benzene, 25° C.: δ=7.84 (br, 4H), 7.67 (d, 3H), 7.34 (d, 3H), 7.13 (br, 4H), 3.68 (m, 1H), 2.41 (br, 8H), 1.63 (br, 2H), 1.30 (br, 9H), 0.93 (br, 2H)

[Preparation Example 4] Preparation of Ligand L4

0.81 g (2.3 mmol) of 3,7-di-tert-butyl-N-isopropyl-5H-benzo[b]phosphindol-5-amine, 2.30 g (22.6 mmol) of triethylamine, and 16 mL of hexane were added to a 100 mL RBF in the glove box, and then the glove box was stored in a refrigerator (−20° C.) for 30 minutes. 1.42 g (2.3 mmol) of chlorobis(4-(tributylsilyl)phenyl)phosphine and 14 mL of hexane were added to a 20 mL glass vial, and then the glass vial was stored in a glove box refrigerator (−20° C.) for 30 minutes. The cooled 20 mL glass vial solution was added all at once to a cooled 100 mL RBF, and then stirring was performed for 15 hours. A solid produced in the reactant was removed by filtration, and a filtrate was dried under vacuum. 30 mL of hexane was added to the dried reactant, stirring was performed for 30 minutes, the mixture was added to a neutral alumina column baked at 150° C. and passed through 120 mL of a solution of hexane:diethyl ether=4:1, and the solution was dried under vacuum to obtain 1.07 g of a transparent oil (ligand L4).

$^1$H NMR (500 MHz), d-benzene, 25° C.: δ=8.07 (br, 4), 7.64 (br, 4H), 7.55 (br, 4H), 7.41 (br, 2H), 2.96 (m, 1H), 1.38 (br, 24H), 1.11 (br, 6H), 0.90 (br, 30H)

[Preparation Example 5] Preparation of Ligand L5

The entire reaction process was performed while the nitrogen atmosphere was maintained. 8.83 g (23.5 mmol) of 1-bromo-2-(2-bromophenyl)naphthalene and 130 mL of diethyl ether were added to a 250 mL RBF, stirring was performed in an acetone/dry ice bath for 30 minutes, and then 19 mL (47.1 mmol) of n-BuLi was added dropwise for 20 minutes. The reactant was stirred at room temperature for 2 hours and stored in a liquid nitrogen bath for 10 minutes, and then 22.6 g (164 mmol) of PCl$_3$ was added dropwise using a dropping funnel. The reaction vessel was taken out of the liquid N$_2$ bath, and stirring was performed at room temperature for 1 hour. The solvent of the reactant was dried under vacuum, the reactant was transferred to a glove box, 30 mL of hexane was added thereto, and stirring was performed for 30 minutes. A bright yellow solid produced was filtered, dried, and dried under vacuum at room temperature for 4 hours, 30 mL of acetonitrile was added thereto, and stirring was performed for 6 hours. A produced white solid was filtered, and dried at room temperature for 15 hours. 5.47 g of the produced white powder (11-chloro-11H-dibenzo[b,g]phosphindole, yield: 82%) was added to a 250 mL RBF in the glove box, 50 mL of hexane was added thereto, stirring was performed at room temperature for 30 minutes, and then 11.4 g (193 mmol) of isopropylamine was added all at once. The reactant was stirred at room temperature for 15 hours to produce a white solid compound, which was removed by filtration, and a filtrate, which was dried under vacuum to obtain 3.83 g of white powder (N-isopropyl-11H-dibenzo[b,g]phosphindol-11-amine, yield: 65%). 0.70 g (2.3 mmol) of N-isopropyl-11H-dibenzo[b,g]phosphindol-11-amine, 2.30 g (22.6 mmol) of triethylamine, and 16 mL of hexane were added to a 100 mL RBF in the glove box, and then the glove box was stored in a refrigerator (−20° C.) for 30 minutes. 0.57 g (2.3 mmol) of chloro-di-o-tolylphosphine and 14 mL of hexane were added to a 20 mL glass vial, and then the glass vial was stored in a glove box refrigerator (−20° C.) for 30 minutes. The cooled 20 mL glass vial solution was added all at once to a cooled 100 mL RBF, and then stirring was performed for 15 hours. A solid produced in the reactant was removed by filtration, and a filtrate was dried under vacuum. 30 mL of hexane was added to the dried reactant, stirring was performed for 30 minutes, the mixture was added to a neutral alumina column baked at 150° C. and passed through 120 mL of a solution of hexane:diethyl ether=4:1, and the solution was dried under vacuum to obtain 0.34 g of a white solid (ligand L5).

$^1$H NMR (500 MHz), d-benzene, 25° C.: δ=7.61 (m, 10H), 7.05 (m, 8H), 3.18 (m, 1H), 2.50 (s, 6H), 0.98 (d, 6H)

[Preparation Example 6] Preparation of Ligand L6

The entire reaction process was performed while the nitrogen atmosphere was maintained. A white solid (ligand L6) was obtained by reaction under the same reaction conditions as Preparation Example 1 (ligand L1), except 2,2'-dibromo-1,1'-biphenyl was used instead of 2,2'-dibromo-4,4'-di-tert-butyl-1,1'-biphenyl.

$^1$H NMR (500 MHz), d-benzene, 25° C.: δ=7.82 (br, 6H), 7.43 (br, 10H), 2.61 (m, 1H), 1.68 (br, 6H), 1.25 (br, 6H)

[Preparation Example 7] Preparation of Ligand L7

The entire reaction process was performed while the nitrogen atmosphere was maintained. A white solid (ligand L7) was obtained by reaction under the same reaction conditions as Preparation Example 1 (ligand L1), except that 2,2'-dibromo-1,1'-biphenyl was used instead of 2,2'-dibromo-4,4'-di-tert-butyl-1,1'-biphenyl, and 1-butylamine was used instead of isopropylamine.

$^1$H NMR (500 MHz), d-benzene, 25° C.: δ=7.83 (d, 6H), 7.05~7.53 (m, 10H), 2.47 (b, 2H), 1.62 (br, 4H), 1.25 (br, 6H), 0.94 (m, 3H)

[Preparation Example 8] Preparation of Ligand L8

The entire reaction process was performed while the nitrogen atmosphere was maintained. A transparent oil (ligand L8) was obtained by reaction in the same reaction conditions as Preparation Example 4 (ligand L4) except that 5-chloro-5H-benzo[b]phosphindol was used instead of 3,7-di-tert-butyl-N-isopropyl-5H-benzo[b]phosphindol-5-amine.

$^1$H NMR (500 MHz), d-benzene, 25° C.: δ=8.17 (br, 4), 7.64~7.80 (br, 10H), 7.35 (br, 4H), 2.92 (m, 1H), 1.38 (br, 24H), 1.11 (br, 6H), 0.89 (br, 30H)

The structures of ligands L1 to L8 prepared above are shown in the following Table 1:

TABLE 1

| entry | Structural formula of ligand |
|---|---|
| L1 | |
| L2 | |
| L3 | |
| L4 | |

TABLE 1-continued

| entry | Structural formula of ligand |
|---|---|
| L5 | (structure shown) |
| L6 | |
| L7 | |
| L8 | |

Preparation of Catalyst System and Ethylene Oligomerization Reaction

Example 1

Preparation of Precursor P1 and Catalyst System (L1-P1+TTB)

The entire process of catalyst preparation was performed in a glove box. 40.0 mg (0.114 mmol) of Cr(acac)$_3$, 16.7 mg (0.114 mmol) of B(Oet)$_3$, 8 g of toluene, and 16.4 mg (0.228 mmol) of THF were added to a 50 mL RBF, and stirring was performed at room temperature for 15 hours. Ligand L1 (0.228 mml) was added to the reaction mixture, and stirring was performed at room temperature for 15 hours. The produced violet solid was filtered and dried under vacuum for 12 hours, and 2 equivalents of trityl tetrakis(pentafluorophenyl)borate (TTB) as a cocatalyst were mixed therewith to prepare a catalyst system (L1-P1+TTB).

Oligomerization Reaction 765 g of methylcyclohexane was added to a 2 L autoclave reactor, and stirring was performed while the internal temperature of the reactor was raised to 35° C. 1200 umol of triethylaluminium (TEAL) was diluted in 6 g of methylcyclohexane, which was added to the reactor, and subsequently 1,000 cc of hydrogen was added thereto. The internal temperature of the reactor was set to 60° C., and then 110,000 cc of ethylene was added to the reactor with stirring. The catalyst system (L1-P1+TTB) prepared above was added to the reactor, and then an oligomerization reaction was performed for 80 minutes. The reaction mixture was cooled, 100 mL of ethanol was added, stirring was performed for 30 minutes, and a reaction solution was filtered under reduced pressure with a paper filter to produce a polymer, which was removed and dried, and the weight of which was measured. A small amount of filtrate was taken and subjected to GC analysis to confirm an oligomer product distribution. The results are shown in the following Table 2.

Example 2

Preparation of Precursor P2 and Catalyst System (L1-P2+TTB)

The entire process of catalyst preparation was performed in a glove box. 40.0 mg (0.114 mmol) of Cr(acac)$_3$, 13.0 mg (0.114 mmol) of AlCl$_3$, 8 g of toluene, and 16.4 mg (0.228 mmol) of THF were added to a 100 mL RBF, and stirring was performed at room temperature for 15 hours. Ligand L1 (0.228 mml) was added to the reaction mixture, and stirring was performed at room temperature for 15 hours. The produced green solid was filtered and dried under vacuum for 12 hours, and 2 equivalents of TTB as a cocatalyst were mixed therewith to prepare a catalyst system (L1-P2+TTB).

Oligomerization Reaction

An oligomerization reaction was performed in the same manner as in Example 1, using the catalyst system (L1-P2+TTB) prepared above, and the results are shown in the following Table 2.

Example 3

Preparation of Precursor P3 and Catalyst System (L1+P3+TTB)

The entire process of catalyst preparation was performed in a glove box. 40.0 mg (0.114 mmol) of Cr(acac)$_3$, 16.7 mg (0.114 mmol) of B(Oet)$_3$, and 8 g of chlorobenzene were added to a 100 mL RBF, and stirring was performed at room temperature for 15 hours. 1.0 umol of a produced green reactant, 2.0 umol of TTB as a cocatalyst, and 1.0 umol of ligand L1 were diluted with 4.0 f of chlorobenzene to prepare a catalyst system (L1+P3+TTB) without further purification.

Oligomerization Reaction

An oligomerization reaction was performed in the same manner as in Example 1, using the catalyst system (L1+P3+TTB) prepared above, and the results are shown in the following Table 2.

Example 4

Preparation of Precursor P1 and Catalyst System (L2-P1+TTB)

The entire process of catalyst preparation was performed in a glove box. 40.0 mg (0.114 mmol) of Cr(acac)$_3$, 16.7 mg (0.114 mmol) of B(Oet)$_3$, 8 g of toluene, and 16.4 mg (0.228 mmol) of THF were added to a 50 mL RBF, and stirring was performed at room temperature for 15 hours. Ligand L2 (0.228 mml) was added to the reaction mixture, and stirring was performed at room temperature for 15 hours. The produced violet solid was filtered and dried under vacuum for 12 hours, and 2 equivalents of TTB as a cocatalyst were mixed therewith to prepare a catalyst system (L2+P1+TTB).

Oligomerization Reaction

An oligomerization reaction was performed in the same manner as in Example 1, using the catalyst system (L2-P1+TTB) prepared above, and the results are shown in the following Table 2.

Example 5

Preparation of Precursor P1 and Catalyst System (L3-P1+TTB)

The entire process of catalyst preparation was performed in a glove box. 40.0 mg (0.114 mmol) of Cr(acac)$_3$, 16.7 mg (0.114 mmol) of B(Oet)$_3$, 8 g of toluene, and 16.4 mg (0.228 mmol) of THF were added to a 50 mL RBF, and stirring was performed at room temperature for 15 hours. Ligand L3 (0.228 mml) was added to the reaction mixture, and stirring was performed at room temperature for 15 hours. The produced violet solid was filtered and dried under vacuum for 12 hours, and 2 equivalents of TTB as a cocatalyst were mixed therewith to prepare a catalyst system (L3-P1+TTB).

Oligomerization Reaction

An oligomerization reaction was performed in the same manner as in Example 1, using the catalyst system (L3–P1+TTB) prepared above, and the results are shown in the following Table 2.

Example 6

Preparation of Precursor P1 and Catalyst System (L4–P1+TTB)

The entire process of catalyst preparation was performed in a glove box. 40.0 mg (0.114 mmol) of Cr(acac)$_3$, 16.7 mg (0.114 mmol) of B(Oet)$_3$, 8 g of toluene, and 16.4 mg (0.228 mmol) of THF were added to a 50 mL RBF, and stirring was performed at room temperature for 15 hours. Ligand L4 (0.228 mml) was added to the reaction mixture, and stirring was performed at room temperature for 15 hours. The produced violet solid was filtered and dried under vacuum for 12 hours, and 2 equivalents of TTB as a cocatalyst were mixed therewith to prepare a catalyst system (L4–P1+TTB).

Oligomerization Reaction

An oligomerization reaction was performed in the same manner as in Example 1, using the catalyst system (L4–P1+TTB) prepared above, and the results are shown in the following Table 2.

Example 7

Preparation of Precursor P1 and Catalyst System (L5–P1+TTB)

The entire process of catalyst preparation was performed in a glove box. 40.0 mg (0.114 mmol) of Cr(acac)$_3$, 16.7 mg (0.114 mmol) of B(Oet)$_3$, 8 g of toluene, and 16.4 mg (0.228 mmol) of THF were added to a 50 mL RBF, and stirring was performed at room temperature for 15 hours. Ligand L5 (0.228 mml) was added to the reaction mixture, and stirring was performed at room temperature for 15 hours. The produced violet solid was filtered and dried under vacuum for 12 hours, and 2 equivalents of TTB as a cocatalyst were mixed therewith to prepare a catalyst system (L5–P1+TTB).

Oligomerization Reaction

An oligomerization reaction was performed in the same manner as in Example 1, using the catalyst system (L5–P1+TTB) prepared above, and the results are shown in the following Table 2.

[Comparative Example 1] MAO Cocatalyst-Applied Oligomerization Reaction

Preparation of Catalyst Cr-L1

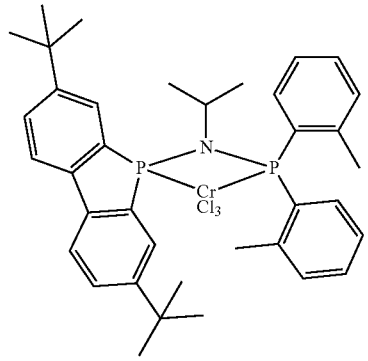

Cr-L1

331 mg (0.88 mmol) of CrCl$_3$(THF)$_3$ and 500 mg (0.88 mmol) of ligand L1 were stirred at 40° C. for 6 hours in 10 mL of an acetonitrile solvent. A produced blue-green solid was filtered and washed with 5 mL of acetonitrile, and the solid remaining after washing was dried under vacuum at room temperature for 15 hours to obtain catalyst Cr-L1 (yield: 87%).

Oligomerization Reaction 765 g of methylcyclohexane was added to a 2 L autoclave reactor, and stirring was performed while the internal temperature of the reactor was raised to 35° C. 1200 umol of TEAL was diluted in 6 g of methylcyclohexane, which was added to the reactor, and subsequently 1,000 cc of hydrogen was added thereto. The internal temperature of the reactor was set to 60° C., and then 110,000 cc of ethylene was added to the reactor with stirring. 600 umol of MAO was diluted in 6 g of methylcyclohexane and added to the reactor, 1 umol of the catalyst Cr-L1 prepared above was diluted with 4.0 g of chlorobenzene and added to the reactor, and then an oligomerization reaction was performed for 80 minutes. The reaction mixture was cooled, 100 mL of ethanol was added, stirring was performed for 30 minutes, and a reaction solution was filtered under reduced pressure with a paper filter to produce a polymer, which was removed and dried, and the weight of which was measured. A small amount of filtrate was taken and subjected to GC analysis to confirm an oligomer product distribution. The results are shown in the following Table 2.

TABLE 2

| | | Oligomerization results | | | | | |
|---|---|---|---|---|---|---|---|
| | | | | | Product: | | |
| | Catalyst system | 1-C8 activity (kg/g-Cr/h) | C6 (wt %) | 1-Hexene in C6 (wt %) | C8 (wt %) | 1-Octene in C8 (wt %) | C10-C14 (wt %) | Polymer (wt %) |
| Example 1 | L1 – P1 + TTB | 41 | 20.3 | 79.3 | 67.9 | >99 | 11.8 | 0.9 |
| Example 2 | L1 – P2 + TTB | 48 | 19.5 | 86.8 | 68.3 | >99 | 12.2 | 1.9 |
| Example 3 | L1 + P3 + TTB | 45 | 19.7 | 87.1 | 69.1 | >99 | 12.2 | 6.3 |
| Example 4 | L2 – P1 + TTB | 48 | 25.3 | 90.3 | 59.3 | >99 | 15.4 | 1.9 |
| Example 5 | L3 – P1 + TTB | 41 | 19.1 | 83.1 | 64.3 | >99 | 16.6 | 0.5 |
| Example 6 | L4 – P1 + TTB | 71 | 20.1 | 85.6 | 64.2 | >99 | 15.7 | 0.3 |
| Example 7 | L5 – P1 + TTB | 39 | 23.8 | 90.1 | 57.8 | >99 | 18.4 | 5.1 |
| Comparative Example 1 | Cr – L1 + MAO | 38 | 21.8 | 89.2 | 59.3 | >99 | 18.9 | 4.3 |

From the oligomerization results of Table 2, it was confirmed that the examples using a catalyst system (L–P+TTB, Examples 1, 2, and 4 to 7) in which a Cr complex (L–P) by a reaction between a catalyst precursor and a phosphine ligand as a catalyst was mixed with an organoboron compound-based cocatalyst, and a catalyst system (L+P+TTB, Example 3) in which the catalyst precursor and a phosphine ligand were mixed to prepare a catalyst (L+P) in-situ which was mixed with an organoboron compound-based cocatalyst showed high 1-$C_8$ preparation activity or had a lower polymer production amount as compared with Comparative Example 1.

In particular, it was confirmed that the catalyst system (L–P+TTB) in which the Cr complex (L–P) as a catalyst was mixed with the organoboron compound-based cocatalyst produced a lower polymer than the catalyst system (L+P+TTB) in which the in-situ catalyst (L+P) and the organoboron compound-based cocatalyst were mixed.

In addition, the 1-C8 preparation activity and the polymer production amount were changed depending on the kind of phosphine ligand, and in particular, when a substituent other than hydrogen is introduced to the benzene ring of a dibenzophosphole moiety of the phosphine ligand (Examples 1, 4, 6, and 7), it was confirmed that high 1-C8 was produced and a lower polymer was produced.

The chromium catalyst precursor according to the present invention is a reaction product of a chromium (III) acetylacetonate and a Lewis acid including a Group 13 element as easily available low-cost raw materials, which may be present in a homogeneous solution phase, so that its storage stability over a long period of time is very good, may be activated later into an organoboron-based cocatalyst as an ethylene oligomerization catalyst with a heteroatom ligand to stably maintain catalytic activity in oligomerization, and is easily applied to a continuous process.

In addition, the ethylene oligomerization catalyst according to the present invention includes a heteroatom ligand having various structures with the chromium catalyst precursor, and forms a catalyst system with an organoboron-based cocatalyst to oligomerize ethylene in-situ, and thus, improves the activity and the selectivity of an ethylene oligomerization reaction to a significantly excellent level without using expensive alkylaluminoxane such as methylaluminoxane (MAO) and modified methylaluminoxane (MMAO) at all, thereby preparing 1-hexene and 1-octene, in particular, 1-octene in a high yield. In addition, since it suppresses the production of an undesired polymer, in particular, a polyethylene (PE) by-product, it does not cause a balloon effect to allow mass production of an ethylene oligomer.

The invention claimed is:

1. A chromium catalyst precursor represented by the following Chemical Formula 1:

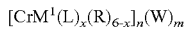 [Chemical Formula 1]

wherein
$M^1$ is a Group 13 element;
L is a ligand in a β-keto enolate form;
R is a halogen, $C_1$-$C_{10}$ alkoxy, or $C_6$-$C_{20}$ aryloxy;
W is a neutral coordination ligand;
n is an integer of 1 or 2;
x is an integer of 1 to 6; and
m is an integer of 2 to 4.

2. The chromium catalyst precursor of claim 1, wherein $M^1$ is boron (B) or aluminum (Al).

3. The chromium catalyst precursor of claim 1, wherein L is an enolate-based ligand represented by the following Chemical Formula A:

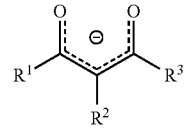

[Chemical Formula A]

wherein
$R^1$ and $R^3$ are independently of each other a halogen, hydrocarbyl, substituted hydrocarbyl, heterohydrocarbyl, or substituted heterohydrocarbyl;
$R^2$ is hydrogen, a halogen, hydrocarbyl, substituted hydrocarbyl, heterohydrocarbyl, or substituted heterohydrocarbyl; and
$R^1$ and $R^2$ or $R^3$ and $R^2$ may be linked by hydrocarbylene, substituted hydrocarbylene, heterohydrocarbylene, or substituted heterohydrocarbylene to form a ring.

4. The chromium catalyst precursor of claim 1, wherein W is a nitrile having 2 to 30 carbon atoms, a cyclic or acyclic ether having 2 to 30 carbon atoms, or water ($H_2O$).

5. The chromium catalyst precursor of claim 4, wherein W is acetonitrile (ACN), tetrahydrofuran (THF), diethyl ether, or water ($H_2O$).

6. The chromium catalyst precursor of claim 1, wherein $M^1$ is boron (B) or aluminum (Al); R is a halogen or $C_1$-$C_{10}$ alkoxy; W is acetonitrile (ACN), tetrahydrofuran (THF), diethyl ether, or water ($H_2O$); m is an integer of 2 to 4; x is an integer of 1 to 6; and L is an acac-based ligand having the following structure:

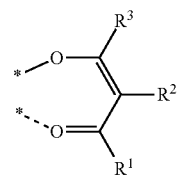

wherein
$R^1$ and $R^3$ are independently of each other $C_1$-$C_{10}$ alkyl or $C_6$-$C_{20}$ aryl, and the alkyl and the aryl of $R^1$ and $R^3$ may be further substituted by one or more substituents selected from halogens, $C_1$-$C_{10}$ alkyl, $C_6$-$C_{20}$ aryl, halo$C_1$-$C_{10}$ alkyl, and halo$C_6$-$C_{20}$ aryl;
$R^2$ is hydrogen, a halogen, $C_1$-$C_{10}$ alkyl, or $C_6$-$C_{20}$ aryl, and the alkyl and the aryl of $R^2$ may be further substituted by one or more selected from halogens, $C_1$-$C_{10}$ alkyl, $C_6$-$C_{20}$ aryl, halo$C_1$-$C_{10}$ alkyl, and halo$C_6$-$C_{20}$ aryl; and
$R^1$ and $R^2$ or $R^3$ and $R^2$ may be linked by $C_3$-$C_{10}$ alkylene, $C_3$-$C_{10}$ alkenylene, $C_6$-$C_{20}$ arylene, $C_3$-$C_{10}$ heteroalkylene, $C_3$-$C_{10}$ heteroalkenylene, or $C_6$-$C_{20}$ heteroarylene to form a ring.

7. The chromium catalyst precursor of claim 6, wherein $M^1$ is boron (B); L is acetylacetonate (ACAC); R is $C_1$-$C_{10}$ alkoxy; W is acetonitrile (ACN), tetrahydrofuran (THF), diethyl ether, or water ($H_2O$); m is an integer of 2 to 4; and x is an integer of 1 to 6.

8. The chromium catalyst precursor of claim 6, wherein $M^1$ is aluminum (Al); L is acetylacetonate (ACAC); R is a halogen; W is acetonitrile (ACN), tetrahydrofuran (THF), diethyl ether, or water (H₂O); m is an integer of 2 to 4; and x is an integer of 1 to 6.

9. An ethylene oligomerization catalyst comprising: a chromium catalyst precursor represented by the following Chemical Formula 1 and a heteroatom ligand represented by the following Chemical Formula 3:

$$[CrM^1(L)_x(R)_{6-x}]_n(W)_m \quad \text{[Chemical Formula 1]}$$

wherein
$M^1$ is a Group 13 element;
L is a ligand in a β-keto enolate form;
R is a halogen, $C_1$-$C_{10}$ alkoxy, or $C_6$-$C_{20}$ aryloxy;
W is a neutral coordination ligand;
n is an integer of 1 or 2;
x is an integer of 1 to 6; and
m is an integer of 2 to 4

$$(R^{12})(R^{11})P-Y-Z \quad \text{[Chemical Formula 3]}$$

wherein
R11 and R12 are independently of each other hydrocarbyl, heterohydrocarbyl, substituted hydrocarbyl, or substituted heterohydrocarbyl;
Y is a linking group between P and Z;
Z is *—P(R13)(R14) or

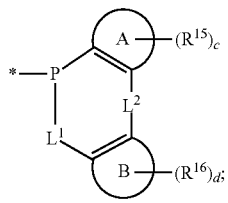

ring A and ring B are independently of each other an aromatic ring;
$L^1$ and $L^2$ are independently of each other a single bond, a heteroatom, a substituted heteroatom, —C(=O)—, or —CR'R"—;
R' and R" are independently of each other hydrogen, hydrocarbyl, substituted hydrocarbyl, heterohydrocarbyl, or substituted heterohydrocarbyl;
R13 to R16 are independently of one another hydrocarbyl, heterohydrocarbyl, substituted hydrocarbyl, or substituted heterohydrocarbyl; and
c and d are independently of each other an integer of 0 to 4.

10. The ethylene oligomerization catalyst of claim 9, wherein
Y is hydrocarbylene, —N($R^{21}$)—, —N($R^{21}$)—N($R^{22}$)—, =C($R^{23}$)—N($R^{21}$)—, —N($R^{21}$)—C($R^{23}$)($R^{24}$)—, or —N($R^{21}$)-$L^3$-N($R^{22}$)—;
$R^{21}$ to $R^{24}$ are independently hydrogen, hydrocarbyl, substituted hydrocarbyl, heterohydrocarbyl, substituted heterohydrocarbyl, or a substituted heteroatom; and
$L^3$ is hydrocarbylene.

11. The ethylene oligomerization catalyst of claim 9, wherein the heteroatom ligand is represented by the following Chemical Formula 4 or 5:

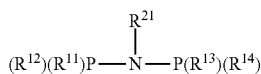

[Chemical Formula 4]

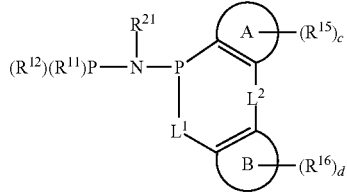

[Chemical Formula 5]

wherein
ring A and ring B are independently of each other a $C_6$-$C_{20}$ aromatic ring;
$R^{11}$ to $R^{14}$, $R^{15}$, and $R^{16}$ are independently of each other $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_1$-$C_{10}$ alkyl, $C_2$-$C_{10}$ alkenyl, $C_2$-$C_{10}$ alkynyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, $C_3$-$C_{10}$ cycloalkyl, mercapto$C_1$-$C_{10}$ alkyl, mercapto$C_2$-$C_{10}$ alkenyl, mercapto$C_2$-$C_{10}$ alkynyl, $C_3$-$C_{20}$ heteroaryl, 5-membered to 7-membered heterocycloalkyl, —N$R^{a1}R^{b1}$ or —Si$R^{c1}R^{d1}R^{e1}$;
$R^{a1}$ and $R^{b1}$ are independently of each other hydrogen, $C_1$-$C_{10}$ alkyl, $C_2$-$C_{10}$ alkenyl, $C_2$-$C_{10}$ alkynyl, $C_6$-$C_{20}$ aryl, $C_1$-$C_{10}$ alkylamino, $C_2$-$C_{10}$ alkenylamino, or $C_2$-$C_{10}$ alkynylamino;
$R^{c1}$ is $C_1$-$C_{10}$ alkyl, $C_2$-$C_{10}$ alkenyl, $C_2$-$C_{10}$ alkynyl, or $C_6$-$C_{20}$ aryl;
$R^{d1}$ and $R^{e1}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;
$R^{21}$ is $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_3$-$C_{10}$ cycloalkyl, $C_3$-$C_{20}$ heteroaryl, 5-membered to 7-membered heterocycloalkyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, —N$R^{a2}R^{b2}$; or —Si$R^{c2}R^{d2}R^{e2}$;
$L^1$ and $L^2$ are independently of each other a single bond, —O—, —S—, —NR'—, —P(=O)R'—, —P(=Se)R'—, —P(=S)R'—, —SiR'R"—, —CR'R"—, or —C(=O)—;
R' and R" are independently of each other hydrogen, $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_3$-$C_{10}$cycloalkyl, $C_3$-$C_{20}$ heteroaryl, 5-membered to 7-membered heterocycloalkyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, —N$R^{a3}R^{b3}$, or —Si$R^{c3}R^{d3}R^{e3}$;
$R^{a2}$, $R^{b2}$, $R^{a3}$, and $R^{b3}$ are independently of one another hydrogen, $C_1$-$C_{10}$ alkyl, $C_2$-$C_{10}$ alkenyl, $C_2$-$C_{10}$ alkynyl, or $C_6$-$C_{20}$ aryl;
$R^{c2}$ and $R^{c3}$ are independently of each other $C_1$-$C_{10}$ alkyl, $C_2$-$C_{10}$ alkenyl, $C_2$-$C_{10}$ alkynyl, or $C_6$-$C_{20}$ aryl;

$R^{d2}$, $R^{e2}$, $R^{d3}$, and $R^{e3}$ are independently of one another hydrogen, $C_1$-$C_{10}$ alkyl, $C_2$-$C_{10}$ alkenyl, $C_2$-$C_{10}$ alkynyl, or $C_6$-$C_{20}$ aryl;

c and d are independently of each other an integer of 0 to 4; and the aryl, the arylalkyl, the alkyl, the arylalkenyl, the alkenyl, the arylalkynyl, the alkynyl, the alkoxy, the aryloxy, the cycloalkyl, the heteroaryl, or the heterocycloalkyl of $R^{11}$ to $R^{14}$, $R^{15}$ and $R^{16}$, and the alkyl, the alkenyl, the aryl, the aralkyl, the aralkenyl, the aralkynyl, the cycloalkyl, the heteroaryl, the heterocycloalkyl, the alkoxy, the aryloxy, the alkoxycarbonyl, the alkylcarbonyloxy, the alkenylcarbonyloxy, the alkynylcarbonyloxy, the aminocarbonyl, the alkylcarbonylamino, the alkenylcarbonylamino, or the alkynylcarbonylamino of $R^{21}$, R', and R" may be further substituted by one or more selected from the group consisting of halogens, $C_1$-$C_{10}$ alkyl, halo$C_1$-$C_{10}$ alkyl, $C_2$-$C_{10}$ alkenyl, $C_2$-$C_{10}$ alkynyl, $C_1$-$C_{10}$ alkoxy, halo$C_1$-$C_{10}$ alkoxy, $C_6$-$C_{20}$ aryl, $C_6$-$C_{20}$ aryloxy, 5-membered to 7-membered heterocycloalkyl, —$NR^{a4}R^{b4}$, and —$SiR^{c4}R^{d4}R^{e4}$; and $R^{a4}$ and $R^{b4}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl, and $R^{c4}$ to $R^{e4}$ are independently of each other $C_1$-$C_{10}$ alkyl or $C_1$-$C_{10}$ alkoxy.

12. The ethylene oligomerization catalyst of claim 11, wherein $L^1$ and $L^2$ are independently of each other a single bond or —O—.

13. The ethylene oligomerization catalyst of claim 12, wherein the heteroatom ligand is represented by the following Chemical Formula 6:

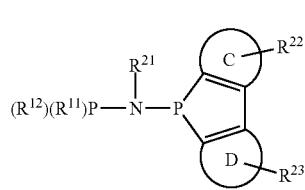

[Chemical Formula 6]

wherein $R^{11}$ and $R^{12}$ are independently of each other $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_1$-$C_{10}$ alkyl, $C_2$-$C_{10}$ alkenyl, $C_2$-$C_{10}$ alkynyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, $C_3$-$C_{10}$ cycloalkyl, mercapto$C_1$-$C_{10}$ alkyl, mercapto$C_2$-$C_{10}$ alkenyl, mercapto$C_2$-$C_{10}$ alkynyl, $C_3$-$C_{20}$ heteroaryl, 5-membered to 7-membered heterocycloalkyl, —$NR^{a1}R^{b1}$ or —$SiR^{c1}R^{d1}R^{e1}$;

$R^{a1}$ and $R^{b1}$ are independently of each other hydrogen, $C_1$-$C_{10}$ alkyl, $C_2$-$C_{10}$ alkenyl, $C_2$-$C_{10}$ alkynyl, $C_6$-$C_{20}$ aryl, $C_1$-$C_{10}$ alkylamino, $C_2$-$C_{10}$ alkenylamino, or $C_2$-$C_{10}$ alkynylamino;

$R^{c1}$ is $C_1$-$C_{10}$ alkyl, $C_2$-$C_{10}$ alkenyl, $C_2$-$C_{10}$ alkynyl, or $C_6$-$C_{20}$ aryl;

$R^{d1}$ and $R^{e1}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;

$R^{21}$ is $C_1$-$C_{10}$ alkyl, $C_2$-$C_{10}$ alkenyl, $C_2$-$C_{10}$ alkynyl, $C_6$-$C_{20}$ aryl, $C_6$-$C_{20}$ aryl$C_1$-$C_{10}$ alkyl, $C_6$-$C_{20}$ aryl$C_2$-$C_{10}$ alkenyl, $C_6$-$C_{20}$ aryl$C_2$-$C_{10}$ alkynyl, $C_3$-$C_{10}$ cycloalkyl, $C_3$-$C_{20}$ heteroaryl, 5-membered to 7-membered heterocycloalkyl, $C_1$-$C_{10}$ alkoxy, $C_6$-$C_{20}$ aryloxy, $C_1$-$C_{10}$ alkoxycarbonyl, $C_1$-$C_{10}$ alkylcarbonyloxy, $C_2$-$C_{10}$ alkenylcarbonyloxy, $C_2$-$C_{10}$ alkynylcarbonyloxy, aminocarbonyl, $C_1$-$C_{10}$ alkylcarbonylamino, $C_2$-$C_{10}$ alkenylcarbonylamino, $C_2$-$C_{10}$ alkynylcarbonylamino, —$NR^{a2}R^{b2}$, or —$SiR^{c2}R^{d2}R^{e2}$;

$R^{a2}$ and $R^{b2}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;

$R^{c2}$ is $C_1$-$C_{10}$ alkyl, $C_2$-$C_{10}$ alkenyl, $C_2$-$C_{10}$ alkynyl, or $C_6$-$C_{20}$ aryl;

$R^{d2}$ and $R^{e2}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl;

ring C and ring D are independently of each other benzene or naphthalene;

$R^{22}$ and $R^{23}$ are hydrogen, $C_1$-$C_{10}$ alkyl, $C_6$-$C_{20}$ aryl, $C_3$-$C_{10}$ cycloalkyl, $C_6$-$C_{20}$ aryl$C_1$-$C_{10}$ alkyl, or $C_1$-$C_{10}$ alkyl$C_6$-$C_{20}$ aryl; and the aryl, the arylalkyl, the alkyl, the arylalkenyl, the alkenyl, the arylalkynyl, the alkynyl, the alkoxy, the aryloxy, the cycloalkyl, the heteroaryl, and the heterocycloalkyl of $R^{11}$ and $R^{12}$, and the alkyl, the alkenyl, the aryl, the aralkyl, the aralkenyl, the aralkynyl, the cycloalkyl, the heteroaryl, the heterocycloalkyl, the alkoxy, the aryloxy, the alkoxycarbonyl, the alkylcarbonyloxy, the alkenylcarbonyloxy, the alkynylcarbonyloxy, the aminocarbonyl, the alkylcarbonylamino, the alkenylcarbonylamino, or the alkynylcarbonylamino of $R^{21}$ may be further substituted by one or more selected from the group consisting of halogens, $C_1$-$C_{10}$ alkyl, halo$C_1$-$C_{10}$ alkyl, $C_2$-$C_{10}$ alkenyl, $C_2$-$C_{10}$ alkynyl, alkoxy, halo$C_1$-$C_{10}$ alkoxy, $C_6$-$C_{20}$ aryl, $C_6$-$C_{20}$ aryloxy, 5-membered to 7-membered heterocycloalkyl, —$NR^{a4}R^{b4}$, and —$SiR^{c4}R^{d4}R^{e4}$; and $R^{a4}$ and $R^{b4}$ are independently of each other hydrogen, $C_1$-$C_{10}$ alkyl, $C_2$-$C_{10}$ alkenyl, $C_2$-$C_{10}$ alkynyl, or $C_6$-$C_{20}$ aryl, and $R^{c4}$ to $R^{e4}$ are independently of each other $C_1$-$C_{10}$ alkyl or $C_1$-$C_{10}$ alkoxy.

14. The ethylene oligomerization catalyst of claim 9, wherein $M^1$ is boron (B) or aluminum (Al); R is a halogen or $C_1$-$C_{10}$ alkoxy; W is acetonitrile (ACN), tetrahydrofuran (THF), diethyl ether, or water ($H_2O$); m is an integer of 2 to 4; x is an integer of 1 to 6; and L is an acac-based ligand having the following structure:

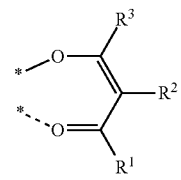

wherein $R^1$ and $R^3$ are independently of each other $C_1$-$C_{10}$ alkyl or $C_6$-$C_{20}$ aryl, and the alkyl and the aryl of $R^1$ and $R^3$ may be further substituted by one or more substituents selected from halogens, $C_1$-$C_{10}$ alkyl, $C_6$-$C_{20}$ aryl, halo$C_1$-$C_{10}$ alkyl, and halo$C_6$-$C_{20}$ aryl;

$R^2$ is hydrogen, a halogen, $C_1$-$C_{10}$ alkyl, or $C_6$-$C_{20}$ aryl, and the alkyl and the aryl of $R^2$ may be further substituted by one or more selected from halogens, $C_1$-$C_{10}$ alkyl, $C_6$-$C_{20}$ aryl, halo$C_1$-$C_{10}$ alkyl, and halo$C_6$-$C_{20}$ aryl; and $R^1$ and $R^2$ or $R^3$ and $R^2$ may be linked by $C_3$-$C_{10}$ alkylene, $C_3$-$C_{10}$ alkenylene, $C_6$-$C_{20}$ arylene, $C_3$-$C_{10}$ heteroalkylene, $C_3$-$C_{10}$ heteroalkenylene, or $C_6$-$C_{20}$ heteroarylene to form a ring.

15. A method of preparing an ethylene oligomer, the method comprising: bringing a catalyst system including the ethylene oligomerization catalyst of claim 9, and an organoboron compound-based cocatalyst into contact with an ethylene monomer to prepare an ethylene oligomer.

16. The method of preparing an ethylene oligomer of claim 15, wherein the organoboron compound-based cocatalyst is an organoboron compound represented by the following Chemical Formula 9:

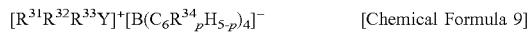
[Chemical Formula 9]

wherein

Y is C or NH;

$R^{31}$ to $R^{33}$ are independently of one another hydrogen, $C_1$-$C_{20}$ alkyl, or $C_6$-$C_{20}$ aryl, and the alkyl or the aryl of $R^{31}$ may be further substituted by one or more selected from the group consisting of $C_1$-$C_{20}$ alkyl and $C_6$-$C_{20}$ aryl;

$R^{34}$ is fluoro, $C_1$-$C_{20}$ alkyl, or $C_1$-$C_{20}$ alkoxy, and the alkyl or the alkoxy of $R^{34}$ may be further substituted by one or more fluoro(s); and p is an integer of 3 to 5.

17. The method of preparing an ethylene oligomer of claim 16, wherein the catalyst system further includes an alkylaluminum compound represented by the following Chemical Formula 10:

[Chemical Formula 10]

wherein $R_{41}$ is $C_1$-$C_{20}$ alkyl; and $R^{42}$ and $R^{43}$ are independently of each other $C_1$-$C_{20}$ alkyl or a halogen.

18. The method of preparing an ethylene oligomer of claim 15, wherein the ethylene oligomer is 1-hexene, 1-octene, or a mixture thereof.

19. The method of preparing an ethylene oligomer of claim 15, wherein a hydrocarbon-based solvent is used as a reaction solvent.

* * * * *

UNITED STATES PATENT AND TRADEMARK OFFICE
CERTIFICATE OF CORRECTION

PATENT NO. : 11,911,749 B2  
APPLICATION NO. : 17/890424  
DATED : February 27, 2024  
INVENTOR(S) : Il Gu Jung et al.

Page 1 of 1

It is certified that error appears in the above-identified patent and that said Letters Patent is hereby corrected as shown below:

In the Claims

Column 35, Line 21, Claim 9, delete "R11 and R12" and insert -- $R^{11}$ and $R^{12}$ --

Column 35, Line 25, Claim 9, delete "*- P(R13)(R14)" and insert -- *-P($R^{13}$)($R^{14}$) --

Column 35, Line 44, Claim 9, delete "R12 to R16" and insert -- $R^{12}$ to $R^{16}$ --

Column 36, Line 46, Claim 11, delete "--$NR^{a2}R^{b2}$;" and insert -- --$NR^{a2}R^{b2}$, --

Column 37, Line 56, Claim 13, delete "--$NR^{a1}R^{b1}$" and insert -- --$NR^{a1}R^{b1}$, --

Column 40, Line 14, Claim 17, delete "$R_{41}$" and insert -- $R^{41}$ --

Signed and Sealed this  
Twenty-third Day of April, 2024

Katherine Kelly Vidal  
*Director of the United States Patent and Trademark Office*